US010511065B2

(12) United States Patent
Shelton, IV et al.

(10) Patent No.: US 10,511,065 B2
(45) Date of Patent: Dec. 17, 2019

(54) BATTERY POWERED SURGICAL INSTRUMENT WITH DUAL POWER UTILIZATION CIRCUITS FOR DUAL MODES

(71) Applicant: ETHICON LLC, Guaynabo, PR (US)

(72) Inventors: Frederick E. Shelton, IV, Hillsboro, OH (US); David C. Yates, West Chester, OH (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 168 days.

(21) Appl. No.: 15/634,452

(22) Filed: Jun. 27, 2017

(65) Prior Publication Data

US 2018/0375165 A1   Dec. 27, 2018

(51) Int. Cl.
*H01M 10/42* (2006.01)
*A61B 17/068* (2006.01)
(Continued)

(52) U.S. Cl.
CPC ....... *H01M 10/4257* (2013.01); *A61B 17/068* (2013.01); *A61B 17/072* (2013.01); *A61B 17/07207* (2013.01); *A61B 17/1155* (2013.01); *G01R 31/382* (2019.01); *H01M 2/1022* (2013.01); *H01M 10/425* (2013.01); *H01M 10/48* (2013.01); *H01M 10/623* (2015.04); *H02J 7/0063* (2013.01); *A61B 2017/00017* (2013.01); *A61B 2017/0023* (2013.01); *A61B 2017/00398* (2013.01);
(Continued)

(58) Field of Classification Search
CPC ............ H01M 10/4257; A61B 17/068; A61B 17/07207; A61B 2017/00017
USPC ......................................................... 429/61
See application file for complete search history.

(56) References Cited

U.S. PATENT DOCUMENTS

| 6,783,524 B2 | 8/2004 | Anderson et al. |
| 7,000,818 B2 | 2/2006 | Shelton, IV et al. |

(Continued)

FOREIGN PATENT DOCUMENTS

EP   2 992 839 A2   3/2016

OTHER PUBLICATIONS

U.S. Appl. No. 15/634,385, filed Jun. 27, 2017.
(Continued)

*Primary Examiner* — James M Erwin
(74) *Attorney, Agent, or Firm* — Frost Brown Todd LLC

(57) ABSTRACT

A battery pack of a surgical instrument includes a battery, a high range monitoring circuit, and a low range monitoring circuit. The high range monitoring circuit is configured to be activated when an electrical current discharged from the battery exceeds a threshold; and to assess the electrical current discharged from the battery at a first rate. The low range monitoring circuit is configured to be activated when the electrical current discharged from the battery is below the threshold; and to assess the electrical current discharged from the battery at a second rate. The battery is configured to conserve power when the low range monitoring circuit is activated. The low range monitoring circuit is configured to increase the second acquisition rate when the low range monitoring circuit remains activated for a predetermined duration. The first rate is greater than the second rate.

20 Claims, 11 Drawing Sheets

(51) Int. Cl.

| | | |
|---|---|---|
| *G01R 31/382* | (2019.01) | |
| *H01M 2/10* | (2006.01) | |
| *H02J 7/00* | (2006.01) | |
| *H01M 10/48* | (2006.01) | |
| *A61B 17/072* | (2006.01) | |
| *H01M 10/623* | (2014.01) | |
| *A61B 17/115* | (2006.01) | |
| *G01R 31/374* | (2019.01) | |
| *G01R 31/36* | (2019.01) | |
| *H01M 16/00* | (2006.01) | |
| *A61B 17/00* | (2006.01) | |
| *A61B 17/11* | (2006.01) | |

(52) U.S. Cl.
CPC ............. *A61B 2017/00464* (2013.01); *A61B 2017/00477* (2013.01); *A61B 2017/00734* (2013.01); *A61B 2017/07257* (2013.01); *A61B 2017/07271* (2013.01); *A61B 2017/07285* (2013.01); *A61B 2017/1132* (2013.01); *G01R 31/3647* (2019.01); *G01R 31/374* (2019.01); *H01M 10/486* (2013.01); *H01M 10/488* (2013.01); *H01M 16/00* (2013.01); *H01M 2010/4271* (2013.01); *H01M 2220/30* (2013.01); *H02J 2007/0067* (2013.01)

(56) References Cited

U.S. PATENT DOCUMENTS

| | | |
|---|---|---|
| 7,342,381 B2 | 3/2008 | Johnson et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,721,930 B2 | 5/2010 | McKenna et al. |
| 8,408,439 B2 | 4/2013 | Huang et al. |
| 8,453,914 B2 | 6/2013 | Laurent et al. |
| 9,072,535 B2 | 7/2015 | Shelton, IV et al. |
| 9,186,142 B2 | 11/2015 | Fanelli et al. |
| 9,421,060 B2 | 8/2016 | Monson et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 2014/0263541 A1 | 9/2014 | Leimbach et al. |
| 2015/0272575 A1 | 10/2015 | Leimbach et al. |
| 2015/0280384 A1 | 10/2015 | Leimbach et al. |
| 2015/0280424 A1* | 10/2015 | Leimbach ............ A61B 17/068 361/18 |
| 2017/0086823 A1 | 3/2017 | Leimbach et al. |

OTHER PUBLICATIONS

U.S. Appl. No. 15/634,418, filed Jun. 27, 2017.
U.S. Appl. No. 15/634,436, filed Jun. 27, 2017.
U.S. Appl. No. 15/634,475, filed Jun. 27, 2017.
U.S. Appl. No. 15/634,497, filed Jun. 27, 2017.
U.S. Appl. No. 15/634,524, filed Jun. 27, 2017.
U.S. Appl. No. 15/634,556, filed Jun. 27, 2017.
U.S. Appl. No. 15/634,589, filed Jun. 27, 2017.
U.S. Appl. No. 15/634,620, filed Jun. 27, 2017.
European Search Report and Written Opinion dated Oct. 1, 2018 for Application No. EP 18180131.7, 8 pgs.
International Search Report and Written Opinion dated Sep. 26, 2018 for Application No. PCT/IB2018/053660, 12 pgs.

* cited by examiner

BATTERY POWERED SURGICAL INSTRUMENT WITH DUAL POWER UTILIZATION CIRCUITS FOR DUAL MODES

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in various ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,000,818, entitled "Surgical Stapling Instrument Having Separate Distinct Closing and Firing Systems," issued Feb. 21, 2006; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014, issued as U.S. Pat. No. 9,186,142 on Nov. 17, 2015; U.S. Patent Application Publication No. 2014/0239041, entitled "Lockout Feature for Movable Cutting Member of Surgical Instrument," Published Aug. 28, 2014, issued as U.S. Pat. No. 9,717,497 on Aug. 1, 2017; U.S. Patent Application Publication No. 2014/0239038, entitled "Surgical Instrument with Multi-Diameter Shaft," published Aug. 28, 2014, issued as U.S. Pat. No. 9,795,379 on Oct. 24, 2017; and U.S. Patent Application Publication No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Applications is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
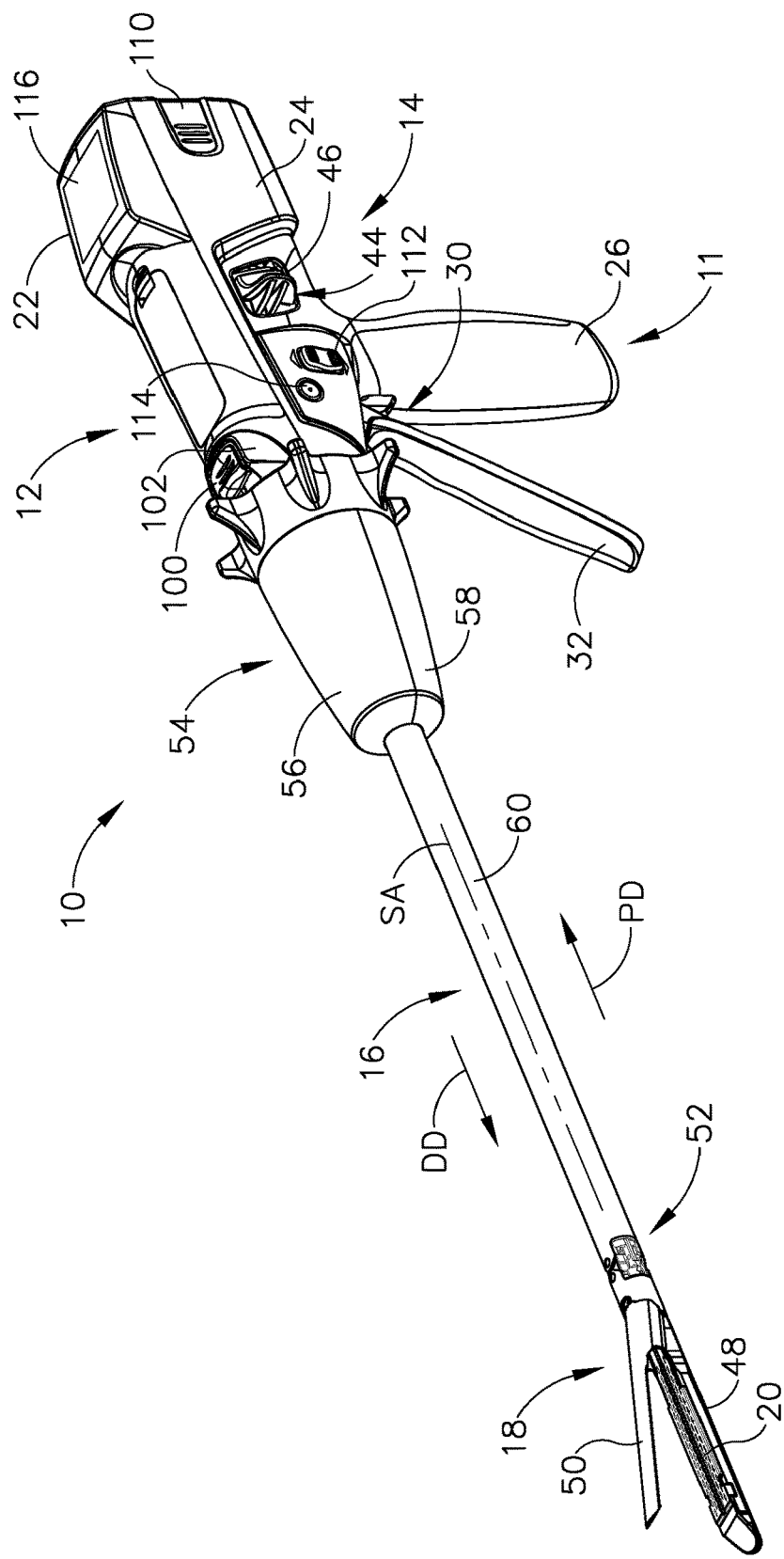
FIG. 1 depicts a perspective view of an exemplary surgical instrument including an interchangeable shaft assembly and a handle assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator. Although the surgical instruments described herein comprise motorized implements for cutting and stapling, it will be appreciated that the configurations described herein may be used with any suitable type of electrical surgical instrument such as cutters, claspers, staplers, RF cutter/coagulators, ultrasonic cutter/coagulators, and laser cutter/coagulators, for example.

I. Overview of Exemplary Surgical Instrument

FIG. 1 depicts a motor-driven surgical cutting and fastening instrument (10) that includes a handle assembly (11) and a removable shaft assembly (16). In some versions, handle assembly (11) and shaft assembly (16) are each provided a single-use, disposable components. In some other versions, handle assembly (11) and shaft assembly (16) are each provided as reusable components. As another merely illustrative example, shaft assembly (16) may be provided as a single-use, disposable component while handle assembly is provided as a reusable component. Various suitable ways in which reusable versions of handle assembly (11) and shaft assembly (16) may be suitable reprocessed for reuse will be apparent to those of ordinary skill in the art in view of the teachings herein.

Handle assembly (11) of the present example includes a housing (12), a closure trigger (32), and a firing trigger (33). At least a portion of housing (12) forms a handle (14) that is configured to be grasped, manipulated and actuated by the clinician. Housing (12) is configured for operative attachment to shaft assembly (16), which has a surgical end effector (18) operatively coupled thereto. As described below, end effector (18) is configured to perform one or more surgical tasks or procedures. In particular, end effector (18) of the example shown in FIG. 1 is operable to perform a surgical cutting and stapling procedure, in a manner similar to an end effector of a conventional endocutter, though it should be understood that this is just one merely illustrative example.

Figure 2:
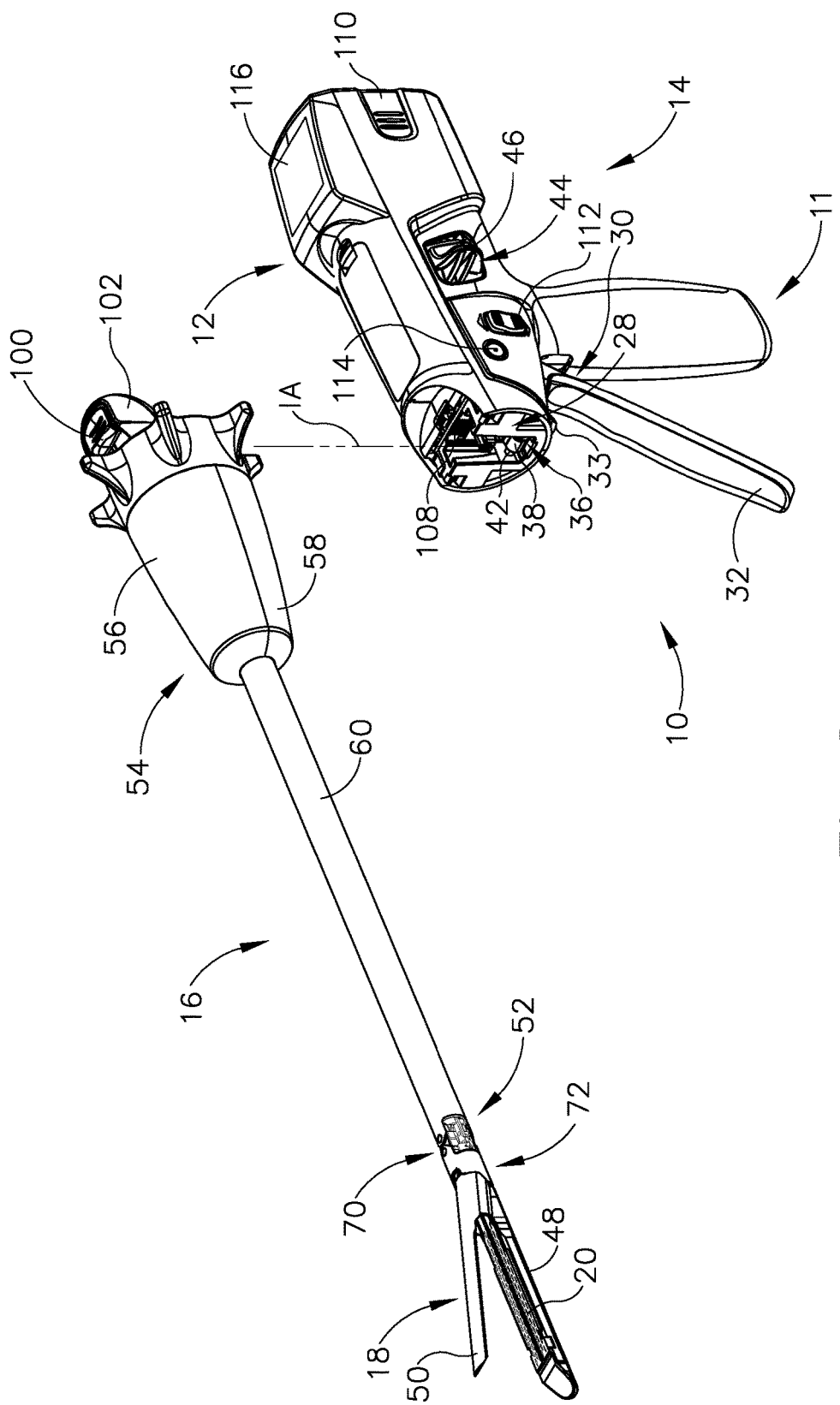
FIG. 2 depicts a perspective view of the instrument of FIG. 1, showing the shaft assembly disassembled from the handle assembly of the instrument.
Figure 3:
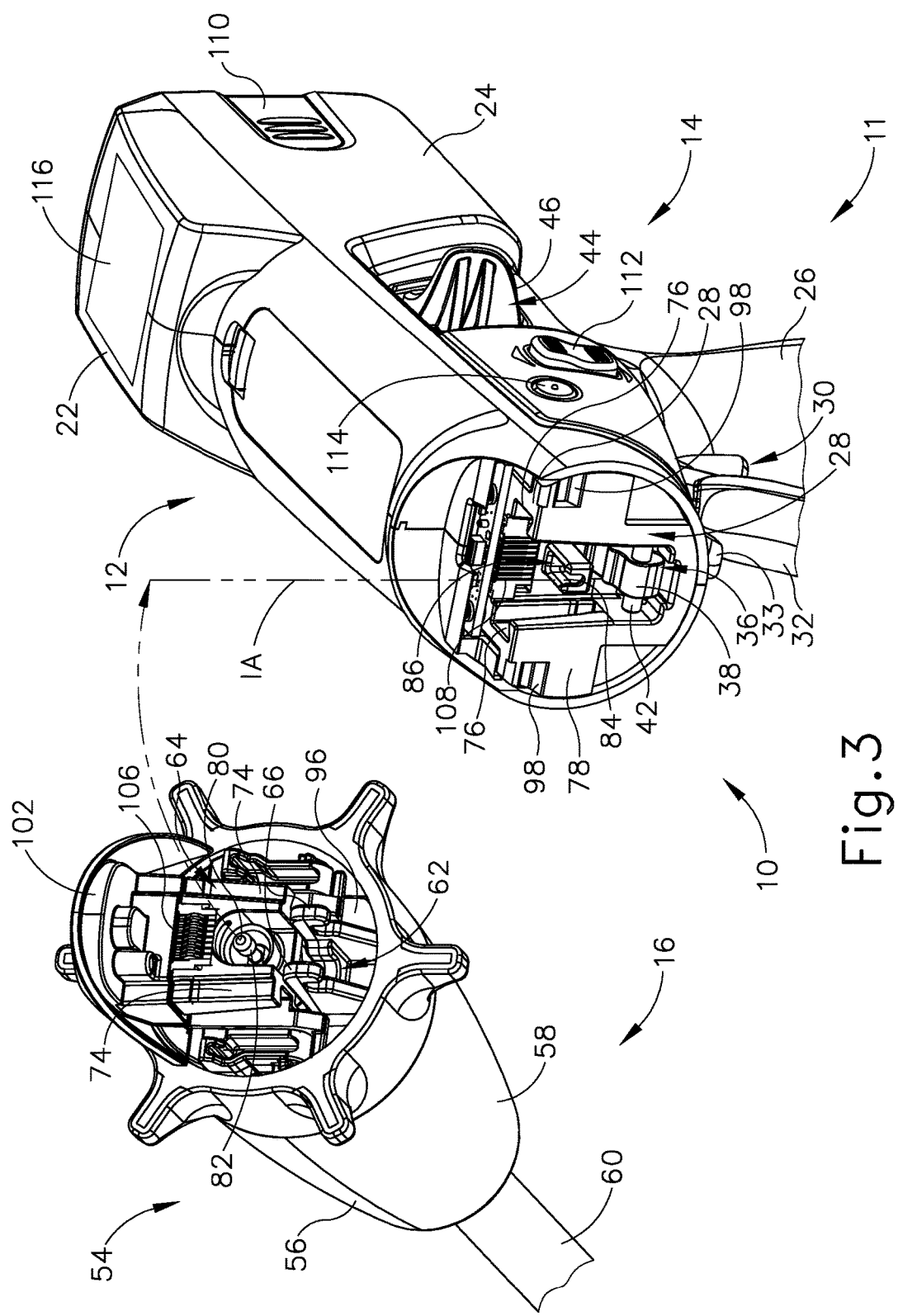
FIG. 3 depicts a partial perspective view of the instrument of FIG. 1, showing the shaft assembly disassembled from the handle assembly of the instrument.

FIG. 1 illustrates surgical instrument (10) with interchangeable shaft assembly (16) operatively coupled to handle assembly (11). FIGS. 2-3 illustrate attachment of interchangeable shaft assembly (16) to housing (12) of handle (14). Handle (14) includes a pair of interconnectable handle housing segments (22, 24) that may be interconnected by screws, snap features, adhesive, etc. In the illustrated arrangement, handle housing segments (22, 24) cooperate to form a pistol grip portion (26) that can be grasped and manipulated by the clinician. As will be discussed in further detail below, handle (14) operatively supports a plurality of drive systems therein that are configured to generate and apply various control motions to corresponding portions of interchangeable shaft assembly (16) that is operatively attached thereto. As will also be discussed in further detail below, triggers (32, 33) are pivotable toward pistol grip portion (26) to activate at least some of the drive systems in handle (14).

Figure 5:
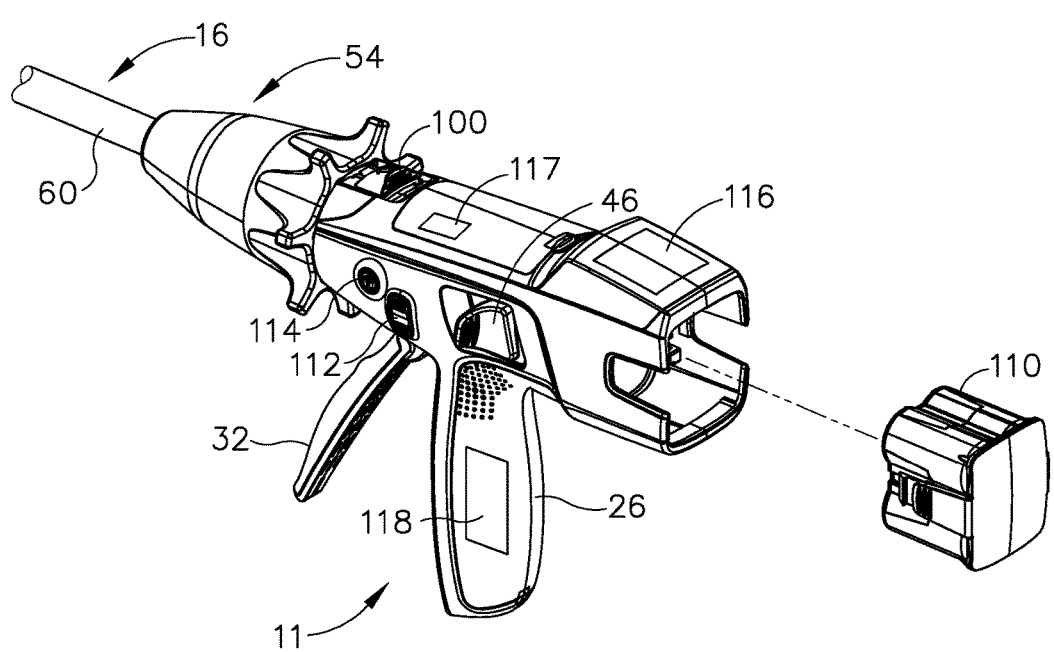
FIG. 5 depicts a perspective view of a proximal portion of the instrument of FIG. 1, with a battery removed from the handle assembly.

At least some of the drive systems in handle assembly (11) are ultimately driven by a motor (118), which is shown schematically in FIG. 5. In the present example, motor (118) is located in pistol grip portion (26), though it should be understood that motor (118) may be located at any other suitable position. Motor (118) receives power from a battery pack (110), which is secured to handle (14). In the present example, and as shown in FIG. 5, battery pack (110) is removable from handle (14). In some other versions, battery pack (110) is not removable from handle (14). In some such versions, battery pack (110) (or a variation thereof) is fully contained within handle housing segments (22, 24). Various suitable forms that motor (118) and battery pack (110) may take will be apparent to those of ordinary skill in the art in view of the teachings herein.

As also shown schematically in FIG. 5, a control circuit (117) is contained within handle (14). By way of example only, control circuit (117) may comprise a microcontroller and/or various other components as will be apparent to those of ordinary skill in the art in view of the teachings herein. Control circuit (117) is configured to store and execute control algorithms to drive motor (118). Control circuit (117) is also configured to drive a graphical user interface (116), which is located at the proximal end of handle assembly (11). In some versions, control circuit (117) is configured to receive and process one or more signals from shaft assembly (16). By way of example only, control circuit (117) may be configured and operable in accordance with at least some of the teachings of U.S. Pub. No. 2015/0272575, entitled "Surgical Instrument Comprising a Sensor System," published Oct. 1, 2015, issued as U.S. Pat. No. 9,913,642 on Mar. 13, 218, the disclosure of which is incorporated by reference herein. Other suitable ways in which control circuit (117) may be configured and operable will be apparent to those of ordinary skill in the art in view of the teachings herein.

As best seen in FIG. 3, a frame (28) of handle (14) operatively supports a plurality of drive systems. In this particular example, frame (28) operatively supports a "first" or closure drive system, generally designated as (30), which may be employed to apply closing and opening motions to interchangeable shaft assembly (16) that is operatively attached or coupled thereto. Also in this particular example, closure drive system (30) includes an actuator in the form of a closure trigger (32) that is pivotally supported by frame (28). More specifically, closure trigger (32) is pivotally coupled to housing (14) by a pin (not shown). Such arrangement enables closure trigger (32) to be manipulated by a clinician such that when the clinician grasps pistol grip portion (26) of handle (14), closure trigger (32) may be easily pivoted from a starting or "unactuated" position (FIG. 4A) toward pistol grip portion (26) to an "actuated" position; and more particularly to a fully compressed or fully actuated position (FIG. 4B). Closure trigger (32) may be biased into the unactuated position by spring or other biasing arrangement (not shown).

In the present example, closure drive system (30) further includes a closure linkage assembly (36) pivotally coupled to closure trigger (32). A portion of closure linkage assembly (36) is shown in FIG. 3. Closure linkage assembly (36) may include a first closure link (not shown) and a second closure link (38) that are pivotally coupled to closure trigger (32) by a pin (not shown). Second closure link (38) may also be referred to herein as an "attachment member" and includes a transverse attachment pin (42). As shown in FIG. 3, attachment pin (42) is exposed when shaft assembly (16) is detached from handle assembly (11). Attachment pin (42) may thus couple with a complementary feature of a shaft assembly (16) when shaft assembly (16) is coupled with handle assembly (11), as described in greater detail below.

Still referring to FIGS. 1-3, first closure link (not shown) is configured to cooperate with a closure release assembly (44) that is pivotally coupled to frame (28). In at least one example, closure release assembly (44) has a release button assembly (46) with a distally protruding locking pawl (not shown) formed thereon. Release button assembly (46) may be pivoted in a counterclockwise direction by a release spring (not shown). As the clinician depresses closure trigger (32) from its unactuated position toward pistol grip portion (26) of handle (14), first closure link (not shown) pivots upwardly to a point where a locking pawl (not shown) drops into retaining engagement with first closure link (not shown), thereby preventing closure trigger (32) from returning to the unactuated position. Thus, closure release assembly (44) serves to lock closure trigger (32) in the fully actuated position.

When the clinician desires to unlock closure trigger (32) from the actuated position to return to the unactuated position, the clinician simply pivots closure release button assembly (46) by urging release button assembly (46) distally, such that locking pawl (not shown) is moved out of engagement with the first closure link (not shown). When the locking pawl (not shown) has been moved out of engagement with first closure link (not shown), closure trigger (32) may return back to the unactuated position in response to a resilient bias urging closure trigger (32) back to the unactuated position. Other closure trigger locking and release arrangements may also be employed.

Interchangeable shaft assembly (16) further includes an articulation joint (52) and an articulation lock (not shown) that can be configured to releasably hold end effector (18) in a desired position relative to a longitudinal axis of shaft assembly (16). In the present example, articulation joint (52) is configured to allow end effector (18) to be laterally deflected away from the longitudinal axis of shaft assembly (16), as is known in the art. By way of example only, end effector (18), articulation joint (52), and the articulation lock (not shown) may be configured and operable in accordance with at least some of the teachings of U.S. Pub. No. 2014/0263541, entitled "Articulatable Surgical Instrument Comprising an Articulation Lock," published Sep. 18, 2014, now abandoned.

In the present example, articulation at articulation joint (52) is motorized via motor (118), based on control input from the operator via an articulation control rocker (112) on handle assembly (11). By way of example only, when the operator presses on the upper portion of articulation control rocker (112), end effector (18) may laterally pivot to the right (viewing instrument (10) from above) at articulation joint (52); and when the operator presses on the lower portion of articulation control rocker (112), end effector (18) may laterally pivot to the left (viewing instrument (10) from above) at articulation joint (52). In some versions, the other side of handle assembly (11) includes another articulation control rocker (112). In such versions, the articulation control rocker (112) on the other side of handle assembly (11) may be configured to provide pivoting of end effector (18) in directions opposite to those listed above in response to upper actuation of articulation control rocker (112) and lower actuation of articulation control rocker (112). By way of example only, articulation control rocker (112) and the rest of the features that provide motorized articulation of end effector (18) at articulation joint (52) may be configured and operable in accordance with at least some of the teachings of U.S. Pub. No. 2015/0280384, entitled "Surgical Instrument Comprising a Rotatable Shaft," published Oct. 1, 2015, issued as U.S. Pat. No. 10,201,364 on Feb. 12, 2019, the disclosure of which is incorporated by reference herein. Other suitable ways in which articulation control rocker (112) and the rest of the features that provide motorized articulation of end effector (18) at articulation joint (52) may be configured and operable will be apparent to those of ordinary skill in the art in view of the teachings herein.

End effector (18) of the present example comprises a lower jaw in the form of an elongated channel (48) that is configured to operatively a support staple cartridge (20) therein. End effector (18) of the present example further includes an upper jaw in the form of an anvil (50) that is pivotally supported relative to elongated channel (48). Interchangeable shaft assembly (16) further includes a proximal housing or nozzle (54) comprised of nozzle portions (56, 58); and a closure tube (60) that can be utilized to close and/or open anvil (50) of end effector (18). Shaft assembly (16) also includes a closure shuttle (62) that is slidably supported within a chassis (64) of shaft assembly (16) such that closure shuttle (62) may be axially moved relative to chassis (64). Closure shuttle (62) includes a pair of proximally-protruding hooks (66) that are configured for attachment to attachment pin (42) that is attached to second closure link (38). A proximal end (not shown) of closure tube (60) is coupled to closure shuttle (62) for relative rotation thereto, though the coupling of closure tube (60) with closure shuttle (62) provides that closure tube (60) and closure shuttle (62) will translate longitudinally with each other. A closure spring (not shown) is journaled on closure tube (60) and serves to bias closure tube (60) in the proximal direction (PD), which can serve to pivot closure trigger (32) into the unactuated position when shaft assembly (16) is operatively coupled to handle (14).

In the present example, articulation joint (52) includes a double pivot closure sleeve assembly (70). Double pivot closure sleeve assembly (70) includes an end effector closure sleeve assembly (72) for engaging an opening tab on anvil (50) in the various manners described in U.S. Pub. No. 2014/0263541, now abandoned, the disclosure of which is incorporated by reference herein. It should be understood that double pivot closure sleeve assembly (70) is coupled with closure tube (60) such that double pivot closure sleeve assembly (70) translates with closure tube (60) in response to pivotal movement of closure trigger (32), even when articulation joint (52) is in an articulated state (i.e., when end effector (18) is pivotally deflected laterally away from the longitudinal axis of shaft assembly (16) at articulation joint (52)). Moreover, the engagement of end effector closure sleeve assembly (72) with anvil (50) provides pivotal movement of anvil (50) toward staple cartridge (20) in response to distal translation of double pivot closure sleeve assembly (70) and closure tube (60); and pivotal movement of anvil (50) away from staple cartridge (20) in response to proximal translation of double pivot closure sleeve assembly (70) and closure tube (60). While shaft assembly (16) of the present example includes articulation joint (52), other interchangeable shaft assemblies may lack articulation capabilities.

As shown in FIG. 3, chassis (64) includes a pair of tapered attachment portions (74) formed thereon that are adapted to be received within corresponding dovetail slots (76) formed within a distal attachment flange portion (78) of frame (28). Each dovetail slot (76) may be tapered or generally V-shaped to seatingly receive attachment portions (74) therein. A shaft attachment lug (80) is formed on the proximal end of an intermediate firing shaft (82). Thus, when interchangeable shaft assembly (16) is coupled to handle (14), shaft attachment lug (80) is received in a firing shaft attachment cradle (84) formed in a distal end of a longitudinal drive member (86). When shaft attachment lug (80) is received in firing shaft attachment cradle (84), intermediate firing shaft (82) will translate longitudinally with longitudinal drive member (86). When intermediate firing shaft (82) translates distally, intermediate firing shaft (82) actuates end effector (18) to drive staples into tissue and cut the tissue, as is known in the art. By way of example only, this actuation of end effector (18) may be carried out in accordance with at least some of the teachings of U.S. Pub. No. 2015/0280384, issued as U.S. Pat. No. 10,201,364 on Feb. 12, 2019, the disclosure of which is incorporated by reference herein; and/or in accordance with the teachings of various other references cited herein.

Figure 4A:
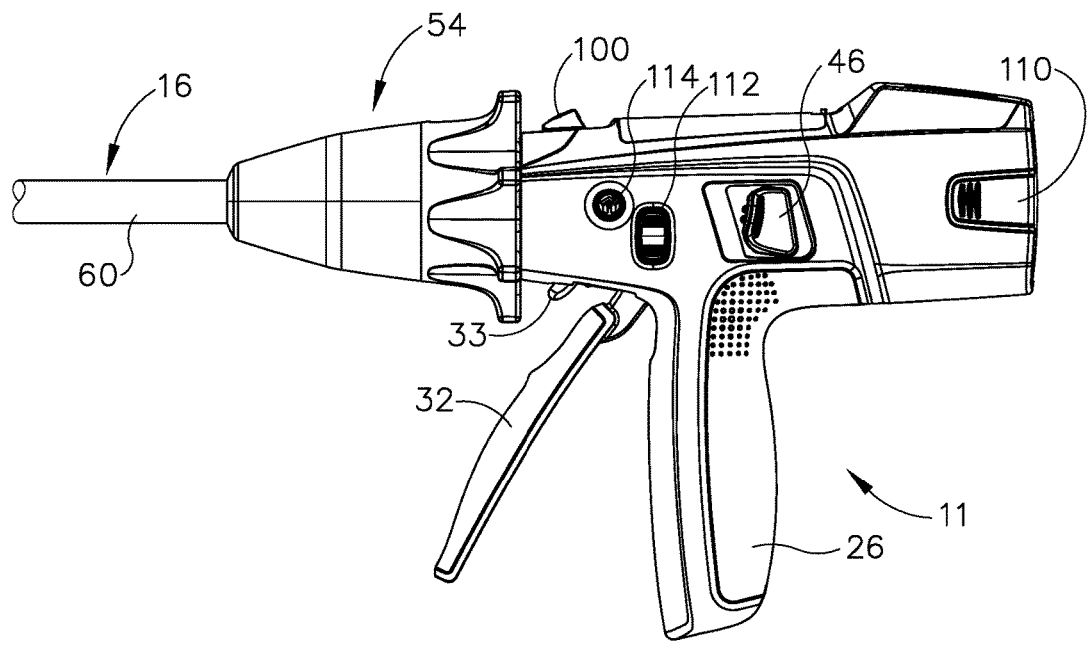
FIG. 4A depicts a side elevational view of a proximal portion of the instrument of FIG. 1, with a closure trigger in a first pivotal position and a firing trigger in a first pivotal position.
Figure 4B:
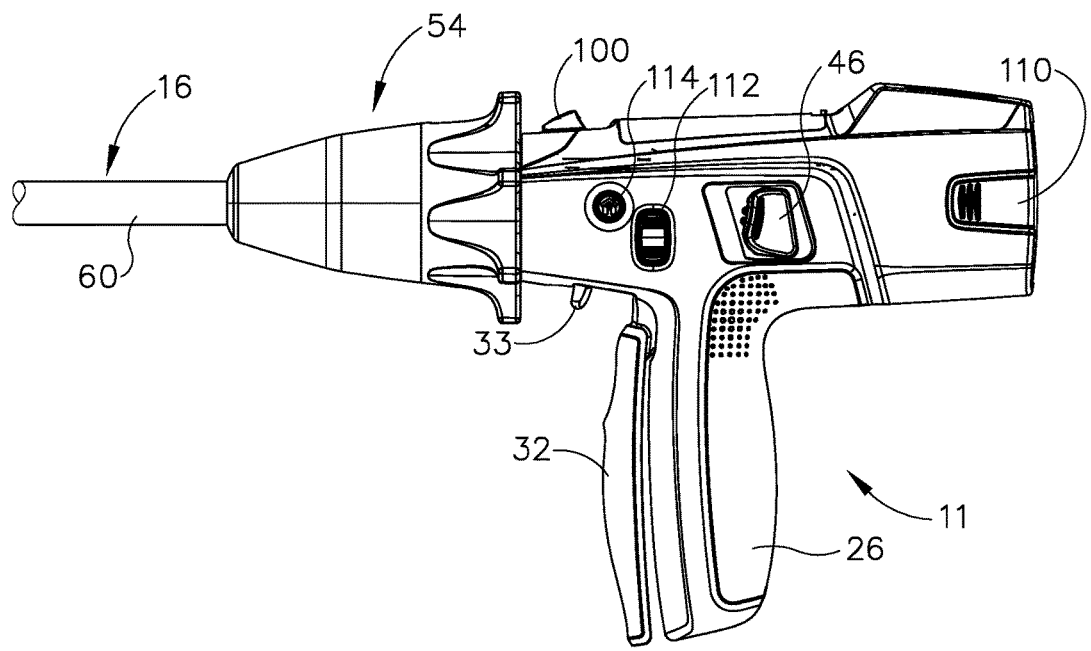
FIG. 4B depicts a side elevational view of a proximal portion of the instrument of FIG. 1, with the closure trigger in a second pivotal position and the firing trigger in a second pivotal position.
Figure 4C:
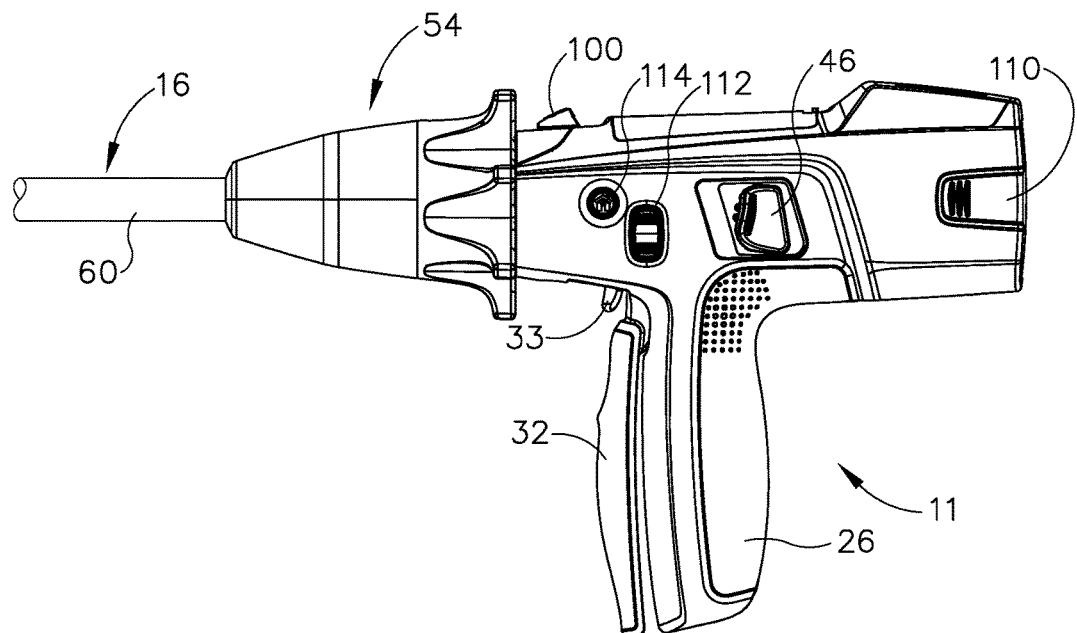
FIG. 4C depicts a side elevational view of a proximal portion of the instrument of FIG. 1, with the closure trigger in the second pivotal position and the firing trigger in a third pivotal position.

FIGS. 4A-4C show the different states of handle assembly (11) during the different states of actuation of end effector (18). In FIG. 4A, handle assembly (11) is in a state where closure trigger (32) is in a non-actuated pivotal position and firing trigger (33) is in a non-actuated pivotal position. At this stage, end effector (18) is in an opened state where anvil (50) is pivoted away from staple cartridge (20).

In FIG. 4B, handle assembly (11) is in a state where closure trigger (32) is in an actuated pivotal position. As noted above, closure trigger (32) will be locked in this position until the operator actuates release button assembly (46). At this stage, end effector is in a closed but unfired state where anvil (50) is pivoted toward staple cartridge (20), such that tissue is being compressed between anvil (50) and cartridge (20). However, firing shaft (82) has not yet been driven distally to actuate staples from staple cartridge (20), and the knife at the distal end of firing shaft (82) has not yet severed the tissue between anvil (20) and staple cartridge (20). It should be noted that firing trigger (33) is in a partially-actuated pivotal position in FIG. 4B, due to the travel of closure trigger (32) from the non-actuated pivotal position to the actuated pivotal position. However, this movement of firing trigger (33) is only provided in order to improve access to firing trigger (33) for the operator. In other words, this movement of firing trigger (33) from the position shown in FIG. 4A to the position shown in FIG. 4B does not yet activate a firing sequence.

In FIG. 4C, handle assembly is in a state where closure trigger (32) remains in the actuated pivotal position, and firing trigger (33) has been pivoted to an actuated pivotal position. This actuation of firing trigger (33) activates motor (118) to drive longitudinal drive member (86) longitudinally, which in turn drives firing shaft (82) longitudinally. The longitudinal movement of firing shaft (82) results in actuation of staples from staple cartridge (20) into the tissue compressed between anvil (50) and staple cartridge (20); and further results in the severing of the tissue compressed between anvil (50) and staple cartridge (20). In some versions, an additional safety trigger is provided. For instance, the additional safety trigger may prevent actuation of firing trigger (33) until the safety trigger is actuated. In other words, after reaching the state shown in FIG. 4B, when the operator is ready to actuate firing trigger (33), the operator must first actuate the safety trigger and then actuate firing trigger (33). It should be understood that the presence of a safety trigger may prevent inadvertent actuation of firing trigger (33).

It should also be understood that, in the present example, the actuation of anvil (50) toward staple cartridge (20) is provided through purely mechanical couplings between closure trigger (32) and anvil (50), such that motor (118) is not used to actuate anvil (50). It should also be understood that, in the present example, the actuation of firing shaft (82) (and, hence, the actuation of staple cartridge (20)) is provided through activation of motor (118). In addition, the actuation of articulation joint (52) is provided through activation of motor (118) in the present example. This motorized actuation of articulation joint (52) is provided via longitudinal translation of drive member (86). A clutch assembly (not shown) within shaft assembly (16) is operable to selectively couple longitudinal translation of drive member (86) with features to either drive articulation joint (52) or actuate staple cartridge (20). Such selective coupling via the clutch assembly is based on the pivotal position of closure trigger (32). In particular, when closure trigger (32) is in the non-actuated position shown in FIG. 4A, activation of motor (118) (in response to activation of articulation control rocker (112)) will drive articulation joint (52). When closure trigger (32) is in the actuated position shown in FIG. 4B, activation of motor (118) (in response to actuation of firing trigger (33)) will actuate staple cartridge (20). By way of example only, the clutch assembly may be configured and operable in accordance with at least some of the teachings of U.S. Pub. No. 2015/0280384, issued as U.S. Pat. No. 10,201,364 on Feb. 12, 2019, the disclosure of which is incorporated by reference herein.

In the present example, handle assembly (11) also includes a "home" button (114). By way of example only, when anvil (50) is in a closed position, "home" button (114) may be operable to activate motor (118) to retract drive member (86) proximally to a proximal-most, "home" position. In addition, or in the alternative, when anvil (50) is in an open position, "home" button (114) may be operable to activate motor (118) to drive articulation joint (52) to achieve a non-articulated state, such that end effector (18) is coaxially aligned with shaft assembly (16). In addition, or in the alternative, "home" button (114) may activate graphical user interface (116) to return to a "home" screen. Other suitable operations that may be provided in response to activation of "home" button (114) will be apparent to those of ordinary skill in the art in view of the teachings herein.

Shaft assembly (16) of the present example further includes a latch system for removably coupling shaft assembly (16) to handle assembly (11) and, more specifically, to frame (28). By way of example only, this latch system may include a lock yoke or other kind of lock member that is movably coupled to chassis (64). As shown in FIG. 3, such a lock yoke may include two proximally protruding lock lugs (96) that are configured for releasable engagement with corresponding lock detents or grooves (98) in frame (28). In some versions, the lock yoke is biased in the proximal direction by a resilient member a spring, etc.). Actuation of the lock yoke may be accomplished by a latch button (100) that is slidably mounted on a latch actuator assembly (102) that is mounted to chassis (64). Latch button (100) may be biased in a proximal direction relative to the lock yoke. The lock yoke may be moved to an unlocked position by urging latch button (100) the in distal direction, which also causes the lock yoke to pivot out of retaining engagement with frame (28). When the lock yoke is in "retaining engagement" with frame (28), lock lugs (96) are retainingly seated within the corresponding lock detents or grooves (98). By way of further example only, shaft assembly (16) may be removably coupled with handle assembly (11) in accordance with at least some of the teachings of U.S. Pub. No. 2017/0086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; in accordance with at least some of the teachings of U.S. Pub. No. 2015/0280384, issued as U.S. Pat. No. 10,201,364 on Feb. 12, 2019, the disclosure of which is incorporated by reference herein; and/or in any other suitable fashion.

To commence the coupling process between shaft assembly (16) and handle assembly (11), the clinician may position chassis (64) of interchangeable shaft assembly (16) above or adjacent to frame (28) such that tapered attachment portions (74) formed on chassis (64) are aligned with dovetail slots (76) in frame (28). The clinician may then move shaft assembly (16) along an installation axis (IA) that is perpendicular to the longitudinal axis of shaft assembly (16) to seat attachment portions (74) in "operative engagement" with the corresponding dovetail receiving slots (76). In doing so, shaft attachment lug (80) on intermediate firing shaft (82) will also be seated in cradle (84) in the longitudinally movable drive member (86) and the portions of pin (42) on second closure link (38) will be seated in the corresponding hooks (66) in closure shuttle (62). As used herein, the term "operative engagement" in the context of two components means that the two components are sufficiently engaged with each other so that upon application of an actuation motion thereto, the components may carry out their intended action, function, and/or procedure.

As discussed above, at least five systems of interchangeable shaft assembly (16) may be operatively coupled with at least five corresponding systems of handle (14). A first system comprises a frame system that couples and/or aligns the frame or spine of shaft assembly (16) with frame (28) of the handle (14). A second system is the latch system that releasably locks the shaft assembly (16) to the handle (14).

A third system is closure drive system (30) that may operatively connect closure trigger (32) of handle (14) and closure tube (60) and anvil (50) of shaft assembly (16). As outlined above, closure shuttle (62) of shaft assembly (16) engages with pin (42) on second closure link (38). Through closure drive system (30), anvil (50) pivots toward and away from staple cartridge (20) based on pivotal movement of closure trigger (32) toward and away from pistol grip (26).

A fourth system is an articulation and firing drive system operatively connecting firing trigger (33) of handle (14) with intermediate firing shaft (82) of the shaft assembly (16). As outlined above, the shaft attachment lug (80) operatively connects with the cradle (84) of the longitudinal drive member (86). This fourth system provides motorized actuation of either articulation joint (52) or staple cartridge (20), depending on the pivotal position of closure trigger (32). When closure trigger (32) is in a non-actuated pivotal position, the fourth system operatively connects articulation control rocker (112) with articulation joint (52), thereby providing motorized pivotal deflection of end effector (18) toward and away from the longitudinal axis of shaft assembly (11) at articulation joint (52). When closure trigger (32) is in an actuated pivotal position, the fourth system operatively connects firing trigger (33) with staple cartridge (20), resulting in stapling and cutting of tissue captured between anvil (50) and staple cartridge (20) in response to actuation of firing trigger (33).

A fifth system is an electrical system that can signal to control circuit (117) in handle (14) that the shaft assembly (16) has been operatively engaged with the handle (14), to conduct power and/or communicate signals between the shaft assembly (16) and the handle (14). In the present example, and as shown in FIG. 3, shaft assembly (16) includes an electrical connector (106) that is operatively mounted to a shaft circuit board (not shown). Electrical connector (106) is configured for mating engagement with a corresponding electrical connector (108) on a handle control board (not shown). Further details regarding the circuitry and control systems may be found in U.S. Pub. No. 2014/0263541, now abandoned, the disclosure of which is incorporated by reference herein and/or U.S. Pub. No. 2015/0272575, issued as U.S. Pat. No. 9,913,642 on Mar. 13, 2018, the disclosure of which is incorporated by reference herein.

Other kinds of systems of interchangeable shaft assembly (16) that may be operatively coupled with at corresponding systems of the handle (14) will be apparent to those of ordinary skill in the art in view of the teachings herein.

As noted above, handle assembly (11) of the present example includes a graphical user interface (116). By way of example only, graphical user interface (116) may be used to display various information about the operational state of battery (110), the operational state of end effector (18), the operational state of articulation joint (52), the operational state of triggers (32, 33), and/or any other kinds of information. Other suitable kinds of information that may be displayed via graphical user interface will be apparent to those of ordinary skill in the art in view of the teachings herein.

Figure 6:
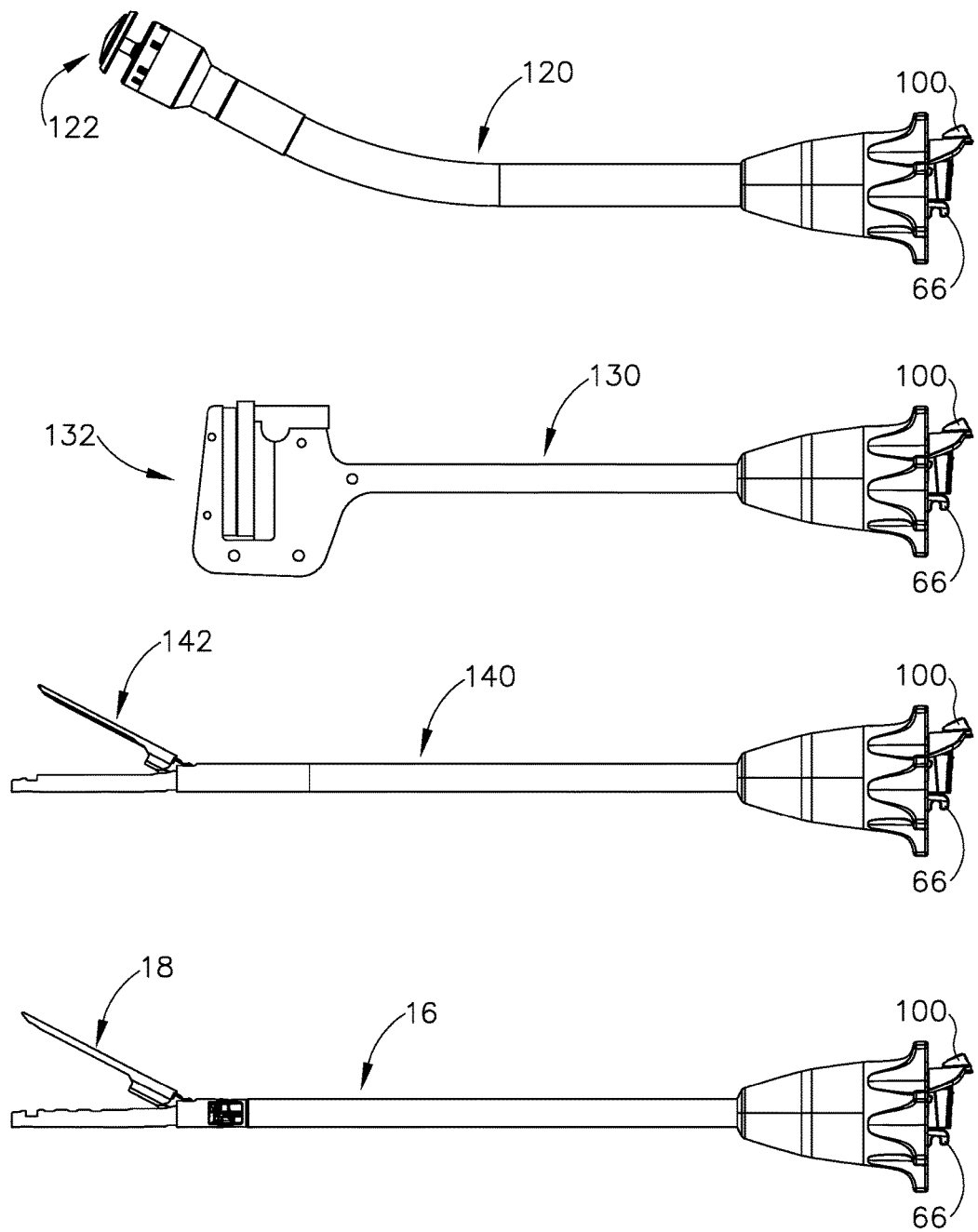
FIG. 6 depicts a side elevational view of an array of alternative shaft assemblies that may be used with the instrument of FIG. 1.

Handle assembly (11) may be configured for use in connection with interchangeable shaft assemblies that include end effectors that are adapted to support different sizes and types of staple cartridges, have different shaft lengths, sizes, and types, etc. By way of example only, FIG. 6 shows various different kinds of shaft assemblies (16, 120, 130, 140) that may be used with handle assembly (11). In particular, FIG. 6 shows a circular stapler shaft assembly (120) with an end effector (122) that is operable to perform a circular stapling operation (e.g., end-to-end anastomosis); a liner stapler shaft assembly (130) with an end effector (132) that is operable to perform a linear stapling operation; and a second endocutter shaft assembly (140) with an end effector (142) that is operable to perform the same kind of stapling and cutting operation as end effector (18). However, in this example, shaft assembly (140) is shorter than shaft assembly (16), shaft assembly (140) has a smaller diameter than shaft assembly (16), and end effector (142) is smaller than end effector (18). It should be understood that these various surgical stapling shaft assemblies (16, 120, 130, 140) are merely illustrative examples.

It should also be understood that control circuit (117) may be configured to detect the kind of shaft assembly (16, 120, 130, 140) coupled with handle assembly (11), and select a control algorithm suited for that particular kind of shaft assembly (16, 120, 130, 140). As another merely illustrative example, each shaft assembly (16, 120, 130, 140) may have a chip or other memory device storing the control algorithm suited for that particular kind of shaft assembly (16, 120, 130, 140); and control circuit (117) may receive and execute that control algorithm after shaft assembly (16, 120, 130, 140) is coupled with handle assembly (11).

In addition, handle assembly (11) may also be effectively employed with a variety of other interchangeable shaft assemblies including those assemblies that are configured to apply other motions and kinds of energy such as, for example, radio frequency (RF) energy, ultrasonic energy and/or motion to end effector arrangements adapted for use in connection with various surgical applications and procedures. Furthermore, end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. Various examples of such cartridges are disclosed in various references that are cited herein.

The various shaft assemblies (16) disclosed herein may employ sensors and various other components that require electrical communication with control circuit (117) in handled assembly (11). The electrical communications may be provided via mating electrical connectors (106, 108). By way of example only, such sensors and other components may be constructed and operable in accordance with at least some of the teachings of U.S. Pub. No. 2015/0272575, issued as U.S. Pat. No. 9,913,642 on Mar. 13, 2018, the disclosure of which is incorporated by reference herein. In addition or in the alternative, instrument (10) may be constructed and operable in accordance with at least some of the teachings of any of the various other references that are cited herein.

It will be appreciated that the various teachings herein may also be effectively employed in connection with robotically-control led surgical systems. Thus, the term "housing" or "body" may also encompass a housing, body, or similar portion of a robotic system that houses or otherwise operatively supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operatively control a surgical instrument. By way of example only, the interchangeable shaft assemblies disclosed herein may be employed with any of the various robotic systems, instruments, components and methods disclosed in U.S. Pat. No. 9,072,535, entitled "Surgical Stapling Instruments with Rotatable Staple Deployment Arrangements," issued Jul. 7, 2015, the disclosure of which is incorporated by reference herein.

II. Exemplary Dual Power Utilization Circuits

In some instances, it may be beneficial for the battery pack and/or other electrical circuit components of a battery powered surgical instrument to be able to monitor the amount of remaining battery power. The battery power monitoring feature may monitor the battery power at different frequencies depending on whether the surgical instrument is in use or not. While the instrument is not in use, the battery power monitoring feature may check the amount of power in the battery less frequently than when the instrument is in active use, to conserve power. Through a power utilization circuit configured to be active when the instrument is not in use, the battery power monitoring feature may monitor the amount of power remaining in the battery on an occasional basis. Once the surgical instrument is in use, the power utilization circuit becomes inactive and a separate power utilization circuit, configured to be active when the instrument is in use, becomes operational. Through the separate power utilization circuit, the remaining battery power of the battery pack is monitored more frequently than the occasional monitoring rate of the other power utilization circuit.

The following description provides various examples of a battery pack with dual power utilization circuits that are configured to monitor the amount of power remaining in the battery pack. The usage of the power utilization circuits may alternate between each power utilization circuit when the battery powered surgical instrument transitions from being in use to being idle, respectively. In particular, the following examples include a high range power utilization circuit that is configured to be active when the surgical instrument is in use and a low range power utilization circuit that is configured to be active when the surgical instrument is not in use. The high range power utilization circuit monitors the remaining amount of power in the battery pack at a high acquisition rate when the surgical instrument is in active use; while the low range power utilization circuit monitors the remaining power of the battery pack at a low acquisition rate when the surgical instrument is not in active use.

The power utilization circuits described below may be used in any of the various battery packs (110) and corresponding surgical instruments (10) described above and in any of the various procedures described in the various references described herein. While the power utilization circuits are physically located within a variation of battery pack (110) in the present example, at least a portion of one or more of the below-described power utilization circuits may instead be located elsewhere within instrument (10) (e.g., within control circuit (117), elsewhere within handle assembly (11), etc.). In addition, while the following examples are provided in the context of surgical instrument (10) described above, the teachings below may be readily incorporated into any other kinds of battery-powered instruments. Other suitable ways in which the below-described power utilization circuits may be used and otherwise carried out will be apparent to those of ordinary skill in the art in view of the teachings herein.

Figure 7:
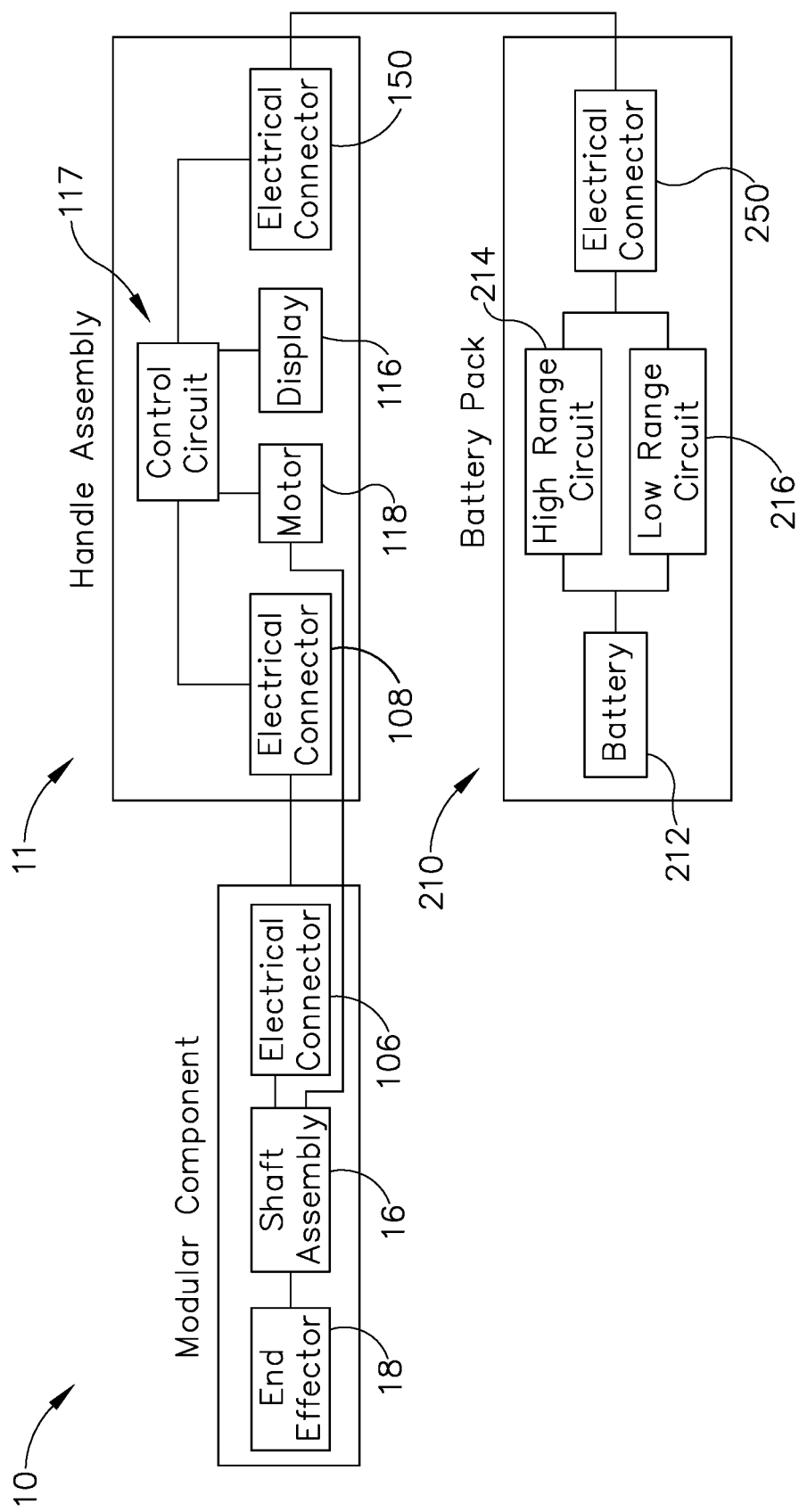
FIG. 7 depicts a block schematic view of the instrument of FIG. 1 connected to an exemplary alternative battery pack.

FIG. 7 shows a block schematic of an exemplary battery pack (210) used with a battery powered surgical instrument (10). Thus, battery pack (210) may be used as a replacement of battery pack (110). In the present example, battery pack (210) includes an electrical connector (250) that is operatively coupled with a high range power utilization circuit (214) and a low range power utilization circuit (216). By way of example only, power utilization circuits (214, 216) may comprise various components as will be apparent to those of ordinary skill in the art in view of the teachings herein. Electrical connector (250) is configured for mating engagement with a corresponding electrical connector (150) of handle assembly (11) of surgical instrument (10). Battery pack (210) further includes a battery (212) electrically coupled to high range power utilization circuit (214) and low range power utilization circuit (216). High range power utilization circuit (214) is configured to store and execute algorithms to electrically monitor the amount of power in battery (212) when surgical instrument (10) is in active use by an operator. Conversely, low range power utilization circuit (216) is configured to store and execute algorithms to electrically monitor the amount of power in battery (212) when surgical instrument (10) is not in active use by an operator. When activated, low range power utilization circuit (216) is configured to conserve the power of battery (212) by placing battery pack (210) in a sleep mode. Once in the sleep mode, low range power utilization circuit (216) limits or stops the power output transmitted to handle assembly (11) since surgical instrument (10) is not in active use.

Power utilization circuits (214, 216) are configured to retrieve measurements of the power drawn from battery (212) to handle assembly (11) to thereby determine whether the measurement exceeds a predetermined power threshold. As further seen in FIG. 7, power utilization circuits (214, 216) of battery pack (210) are in electrical communication with control circuit (117) of handle assembly (11) through the mating engagement of electrical connectors (150, 250). As noted above, control circuit (117) is configured to store and execute algorithms to process signals from shaft assembly (16) and to drive motor (118). Upon receiving an electrical signal (not shown) that shaft assembly (16) has been operatively engaged, control circuit (117) communicates the signal to battery pack (210) in order to draw power from battery (212) and thereby drive motor (118). As power is drawn from battery (212) the level of electrical current surpasses the power threshold of low range power utilization circuit (216), thereby deactivating low range power utilization circuit (216) and activating high range power utilization circuit (214).

Once high range power utilization circuit (214) is activated, high range power utilization circuit (214) continuously monitors the active use of battery (212) by handle assembly (11) at a programmed, rapid acquisition rate. As a merely illustrative example, high range power utilization circuit (214) may have a rapid acquisition rate ranging from 1 measurement every second to 2000 measurements every second. Through the data collected by high range power utilization circuit (214) as power is actively drawn from battery (212) to operate motor (118), high range power utilization circuit (214) calculates the remaining charge of battery (212). For instance, in versions where battery (212) comprise a lithium battery, the temperature of battery (212) and the current draw or rate at which battery (212) is expended may be directly related to the efficiently of the electrolytes and electrodes that remain. By way of further example only, if a CR123a lithium battery has 1550 MAh capacity and it has a 5 A draw, the resulting capacity may be closer to 800 MAh, due to the current draw rate. Temperature may also vary the remaining charge greatly, and a higher power draw rate may change battery (212) temperature relative to ambient temperature as well. These relationships for this type of battery (212) are well known so if high range power utilization circuit (214) can measure temperature, current draw, and power expenditure, then high range power utilization circuit (214) can accurately calculate remaining capacity In some versions, the rapid acquisition rate of high range power utilization circuit (214) may be scaled in relation to the power drawn from battery (212) by motor (118) and/or other components of handle assembly (11) when instrument (10) is in a state of active use. For instance, high range power utilization circuit (214) may be configured to reduce the rapid acquisition rate as the amount of power drawn from battery (212) increases. Alternatively, the rapid acquisition rate may increase as the amount of power drawn from battery (212) increases.

Although not shown, it should be understood that power utilization circuits (214, 216) may be positioned within handle assembly (11), for example in control circuit (117), instead of within battery pack (210). In this instance, the coupling of handle assembly (11) and battery pack (210) through electrical connectors (150, 250) allows power utilization circuits (214, 216) to monitor the remaining power of battery (212) despite power utilization circuits (214, 216) not being physically located within battery pack (210).

In the present example, high range power utilization circuit (214) is configured to continuously monitor the power drawn from battery (212) at the rapid acquisition rate until control circuit (117) stops transmitting the electrical signal (not shown) to battery pack (210) that shaft assembly (16) is operatively engaged and requires power. In this instance, since handle assembly (11) no longer draws power from battery (210) the amount of power drawn from battery (212) falls below the predetermined power threshold of high range power utilization circuit (214), thus deactivating high range power utilization circuit (214). Further, low range power utilization circuit (216) simultaneously detects the low amount of power transmitted from battery (212) to handle assembly (11), which now falls within the predetermined power threshold of low range power utilization circuit (216), and thus causes low range power utilization circuit (216) to become active.

Once activated, low range power utilization circuit (216) continuously monitors the power drawn from battery (212) at a programmed, slow acquisition rate to occasionally calculate the remaining amount of power in battery (212). In some versions, low range power utilization circuit (216) monitors the internal discharge rate of battery (212), the ambient temperature, and the time between uses of battery (212). As a merely illustrative example, low range power utilization rate (216) may have a slow acquisition rate ranging from 1 measurement every minute to 1 measurement every hour. In some versions, the slow acquisition rate of low range power utilization circuit (216) may be scaled and increased in relation to the duration since high range power utilization circuit (214) was last activated. For exemplary purposes, the slow acquisition rate may decrease from 1 measurement every minute to 1 measurement every ten minutes after a predetermined period, for instance three days, has elapsed since the level of power drawn from battery (212) exceeded the power threshold of low range power utilization circuit (216).

In addition to the initial reduction of the slow acquisition rate of low range power utilization circuit (216), the slow acquisition rate may decrease further, for instance from 1 measurement every ten minutes to 1 measurement every hour, after a continued period where handle assembly (11) fails to draw power from battery (212). For example, such subsequent decrease in the slow acquisition rate may take effect after an additional three days since the initial three-day period of nonactivity by handle assembly (11) has elapsed. Although not shown, power utilization circuits (214, 216) of battery pack (210) may include a clock to calculate the elapsed duration between high levels of power drawn from battery (212). Various suitable time measuring devices that power utilization circuits (214, 216) may incorporate will be apparent to those of ordinary skill in the art in view of the teachings herein.

Low range power utilization circuit (216) is configured to continuously monitor the amount of power drawn from battery (212) until control circuit (117) begins transmitting the electrical signal (not shown) to battery pack (210) that shaft assembly (16) is operatively engaged and requires power. Since handle assembly (11) will once again require power from battery pack (210) to drive motor (118), the amount of power drawn from battery (212) will increase and exceed the predetermined power threshold of low range power utilization circuit (216). The increase in power drawn from battery (212) will thereby deactivate low range power utilization circuit (216) and reactivate high range power utilization circuit (214) such that the remaining amount of power in battery (212) will be evaluated at the rapid acquisition rate.

In the present example, high range power utilization circuit (214) may be configured to activate when the level of current drawn from battery (212) is in a relatively high range. For example, at the low end of the high range, high range power utilization circuit (214) may be programmed to activate when detecting a current draw from battery (212) as low as 0.005 amperes, for instance when powering graphical user interface (116), control circuit (117), or other electrically powered components of handle assembly (11) excluding motor (118). At the high end of the high range, high range power utilization circuit (214) may be further programmed to active when detecting a current draw from battery (212) as high as 6.000 amperes, for instance when powering motor (118). Conversely, low range power utilization circuit (216) may be configured to detect a small predetermined threshold of current draw from battery (212) to handle assembly (11). For exemplary purposes only, low range power utilization circuit (216) may be programmed to activate when detecting a current draw from battery (212) in a range between 0.000001 amperes to 0.0001 amperes, for instance when handle assembly (11) is in sleep mode and graphical user interface (116), control circuit (117) and motor (118) are not in use.

The predetermined threshold amounts may be directly programmed in power utilization circuits (214, 216) in accordance with the particular surgical instrument (10) that battery pack (210) will be utilized with. Alternatively, control circuit (117) of handle assembly (11) may be programmed to communicate the predetermined threshold amounts of power to power utilization circuits (214, 216) once handle assembly (11) and battery pack (210) are electrically coupled. Other suitable ways in which the predetermined threshold amounts for high range power utilization circuit (214) and low range power utilization circuit (216) may be programmed will be apparent to those of ordinary skill in the art in view of the teachings herein. It should be understood that the predetermined threshold amounts for power utilization circuits (214, 216) may vary based on the type of shaft assembly (16, 120, 140) that is coupled to handle assembly (11). Thus, power utilization circuits (214, 216) may be configured to be programmed on an ad hoc basis by control circuit (117) after control circuit (117) determines the type of shaft assembly (16, 120, 140) that is coupled to handle assembly (11).

Figure 8:
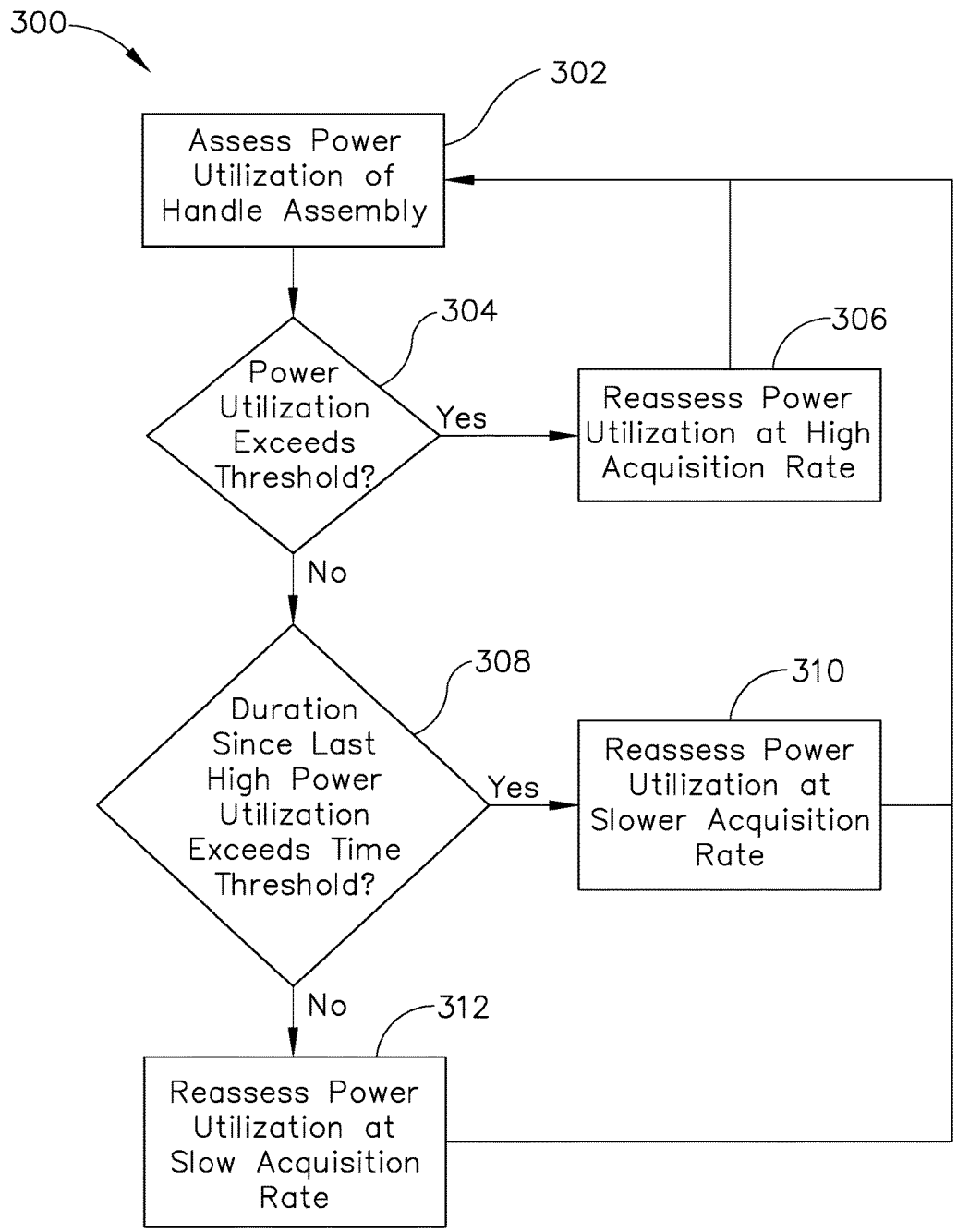
FIG. 8 depicts a flow diagram illustrating an algorithim utilizied by the battery pack of FIG. 7 when determining which power monitoring circuit to activate.

FIG. 8 shows a flow diagram illustrating steps of an exemplary method (300) that may be used to assess the level of current output from battery (212), or the power drawn by handle assembly (11), in a manner consistent with the disclosure above. The method (300) may be performed with battery pack (210) or any suitable variation thereof. As described above, battery pack (210) comprises a high range power utilization circuit (214) and low range power utilization circuit (216). At step (302), power utilization circuits (214, 216) assess the power utilization of handle assembly (11) from battery (212), for example in the manner described above. At step (304), power utilization circuits (214, 216) then determine whether the current output from battery (212) to handle assembly (11) exceeds the power threshold of low range power utilization circuit (216), thereby being within the power threshold range of high range power utilization circuit (214), or remains within the power threshold range of low range power utilization circuit (216). If the power utilization does exceed the threshold of low range power utilization circuit (216), the system may proceed to step (306) where high range power utilization circuit (214) will activate and apply the high acquisition rate when reassessing the power utilization of handle assembly (11) at step (302).

Alternatively, at step (308), where the power utilization does not exceed the threshold of low range power utilization circuit (216), the system may determine the elapsed duration since the power utilization last exceeded the threshold range of low range power utilization circuit (216). If the duration exceeds the programmed time threshold then low range power utilization circuit (216) will reassess the power utilization by handle assembly (11) at a slower acquisition rate than a default slow acquisition rate, as seen in step (310). Alternatively, at step (312), where the elapsed duration since high range power utilization circuit (214) was last activated does not exceed the programmed time threshold, low range power utilization circuit (216) will reassess the current output from battery (212) at the default slow acquisition rate.

Methods of assessing the power utilization by handle assembly (11), measuring the duration since the power utilization by handle assembly (11) last exceeded a time threshold, and determining the rate at which the power utilization of handle assembly (11) is reassessed have been described above in connection with the specified power utilization circuits (214, 216) of battery pack (210). However, persons skilled in the art will appreciate that the methods described above may be adapted as appropriate to similarly assess the level of power output from battery (212) in substitute of measuring the level of power usage by handle assembly (11). As it would be apparent to those of ordinary skill in the art in view of the teachings herein, either reference point for measure will be appropriate in performing the methods described.

Figure 11:
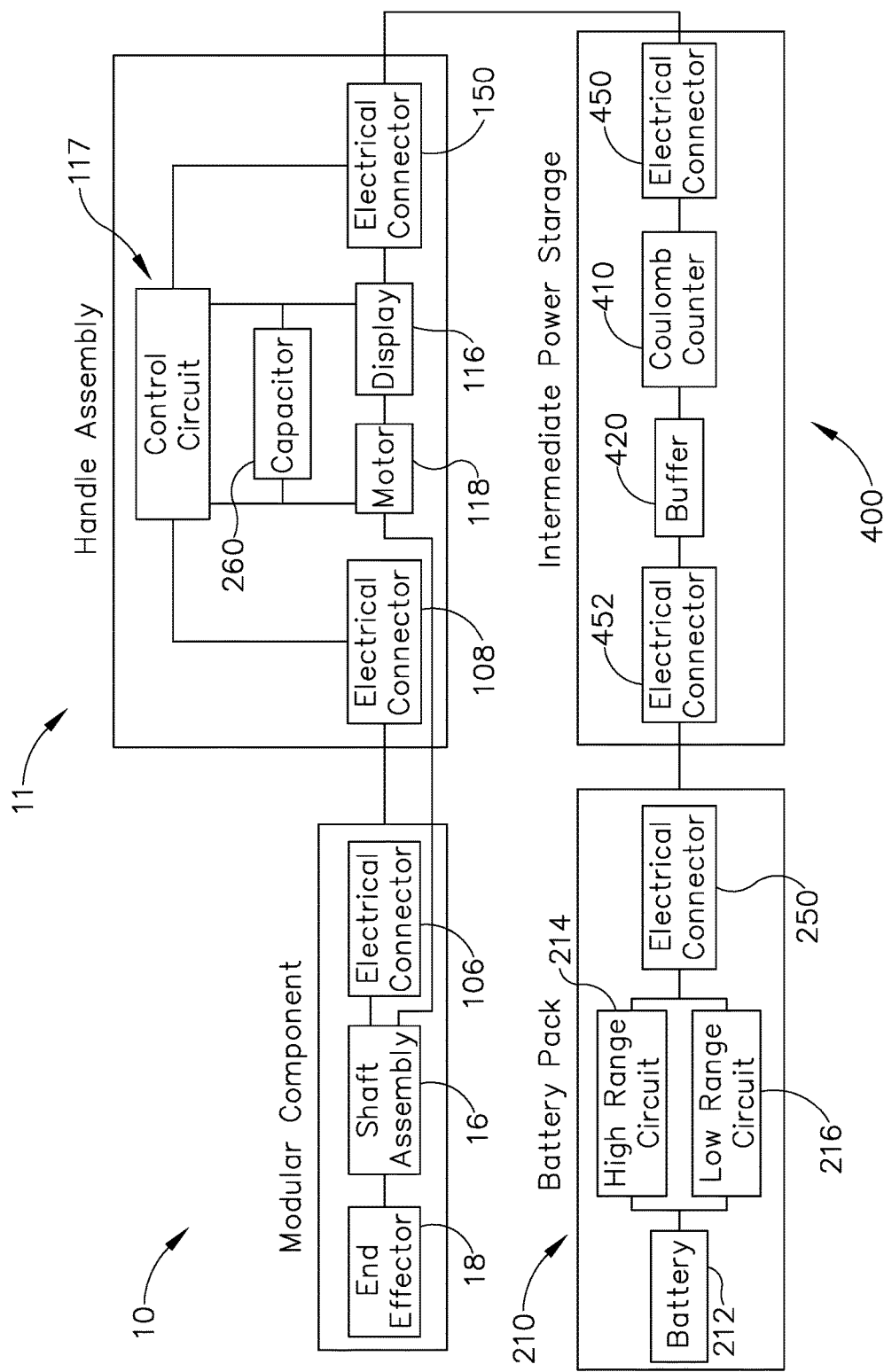
FIG. 11 depicts a block schematic view of the intermediate power storage device of FIG. 9 interconnected between an exemplary variation of the instrument of FIG. 1 and the battery pack of FIG. 7, with the instrument including a capacitor.

As seen in FIG. 11, handle assembly (11) may further include a capacitor (260) in parallel connection between control circuit (117) and motor (118). In this instance, capacitor (260) becomes charged as battery (212) provides a high amount of power to handle assembly (11). The amount of charge that is built up in capacitor (260) will correspond with the power drawn by the electrically powered components of handle assembly (11) (e.g., motor (118), graphical user interface (116), control circuit (117), etc.). Thus, the amount of charge present in capacitor (260) will be representative of the power drawn by the electrically powered components of handle assembly (11). Thus, by checking the charge of the capacitor after articulation of end effector (18) or firing of end effector (18), high range power utilization circuit (214) may determine the amount of current drawn from battery (212) to operate handle assembly (11) and thereby measure the remaining amount of power in battery (212). This alternative method of measuring the remaining charge of battery (212) may be beneficial as it may require less power by high range power utilization circuit (214) to determine the voltage balance of battery (212). In other words, the measurements of the remaining charge of battery (212) occur on an ad hoc basis, rather than at a prearranged acquisition rate, which may ultimately draw less power from battery (212) and extend the lifespan of battery pack (212).

Furthermore, low range power utilization circuit (216) may be configured to routinely measure a temperature of battery (212). In such versions, identifying the temperature of battery (212) allows low range power utilization circuit (216) to more accurately determine the remaining charge of battery (212). A relatively high or relatively low temperature of battery (212) may lead to a relatively shorter life of battery (212), particularly if battery (212) encounters such high or low temperatures for a prolonged period of time. Low range power utilization circuit (216) may factor the temperature data collected from battery (212) when calculating the remaining amount of power in battery (212). In addition, the temperature of battery (212) may be measured by low range power utilization circuit (216) at the slow acquisition rate defined above.

As another merely illustrative example, to the extent that battery (212) is subject to the relatively low draw of internal discharge rather than a usage discharge when low range power utilization circuit (216) is active, low range power utilization circuit (216) could utilize a simple counter or clock that is used to estimate the loss of power while battery (212) is being sterilized and shelved. In particular, low range power utilization circuit (216) may simply track the time between uses and the internal discharge rate to approximate the shelf life of battery (212) rather than measuring the shelf life of battery (212).

III. Exemplary Intermediate Power Storage Device

In some instances, it may be beneficial for a battery powered surgical instrument (10) to incorporate an intermediate power storage device that is capable of evaluating the power remaining in battery pack (210); and providing enough power to alert the operator when battery pack (210) no longer contains the minimum amount of power necessary for the surgical instrument (10) to complete a critical function (e.g., activate motor 018) long enough to complete a full actuation stroke). Due to the variable functions that surgical instrument (10) may be used, it may be difficult to anticipate when battery (212) will become completely exhausted. Without any indication of when a power shortage may occur, it may be likely for surgical instrument (10) to attempt to perform a critical function when insufficient power exists in battery (212) to complete the function.

The intermediate power storage, positioned between battery (212) and control circuit (117), may measure the remaining power contained in battery pack (210) to ensure a sufficient amount of electrical charge exists in battery (212) for the successful and complete operation of surgical instrument (10). Once the intermediate power storage verifies that the minimum amount of power necessary does exist in battery pack (210), the intermediate power storage may indicate to the operator that sufficient charge exists for the successful actuation of surgical instrument (10).

Once surgical instrument (10) is actuated, the intermediate power storage may reassess the charge of battery (212) for a subsequent actuation by surgical instrument (10). In the instance where battery (212) does not contain the minimum amount of power necessary to operate surgical instrument (10), a display may indicate to the operator that battery (212) is insufficient to complete an additional actuation of surgical instrument (10). Such display indicator may be transmitted from the intermediate power storage to graphical user interface (116) of surgical instrument (10). Providing the intermediate power storage device allows an operator to manage the status of the remaining battery power and ensure both safety and effectiveness when operating surgical instrument (10).

The following description provides various examples of an intermediate power storage electrically coupled to battery pack (110, 210) and surgical instrument (10) and configured to verify a sufficient amount of charge exists in battery pack (110, 210) prior to the actuation of surgical instrument (10). In particular, the following examples include an intermediate power storage containing a coulomb counter configured to accurately measure the power drawn from the battery (212) during use of surgical instrument (10). It should be understood that the intermediate power storage described below may be used in any of the various battery packs (110, 210) and corresponding surgical instruments (10) described above and in any of the various procedures described in the various references described herein. Other suitable ways in which the below-described intermediate power storage may be used will be apparent to those of ordinary skill in the art in view of the teachings herein.

Figure 9:
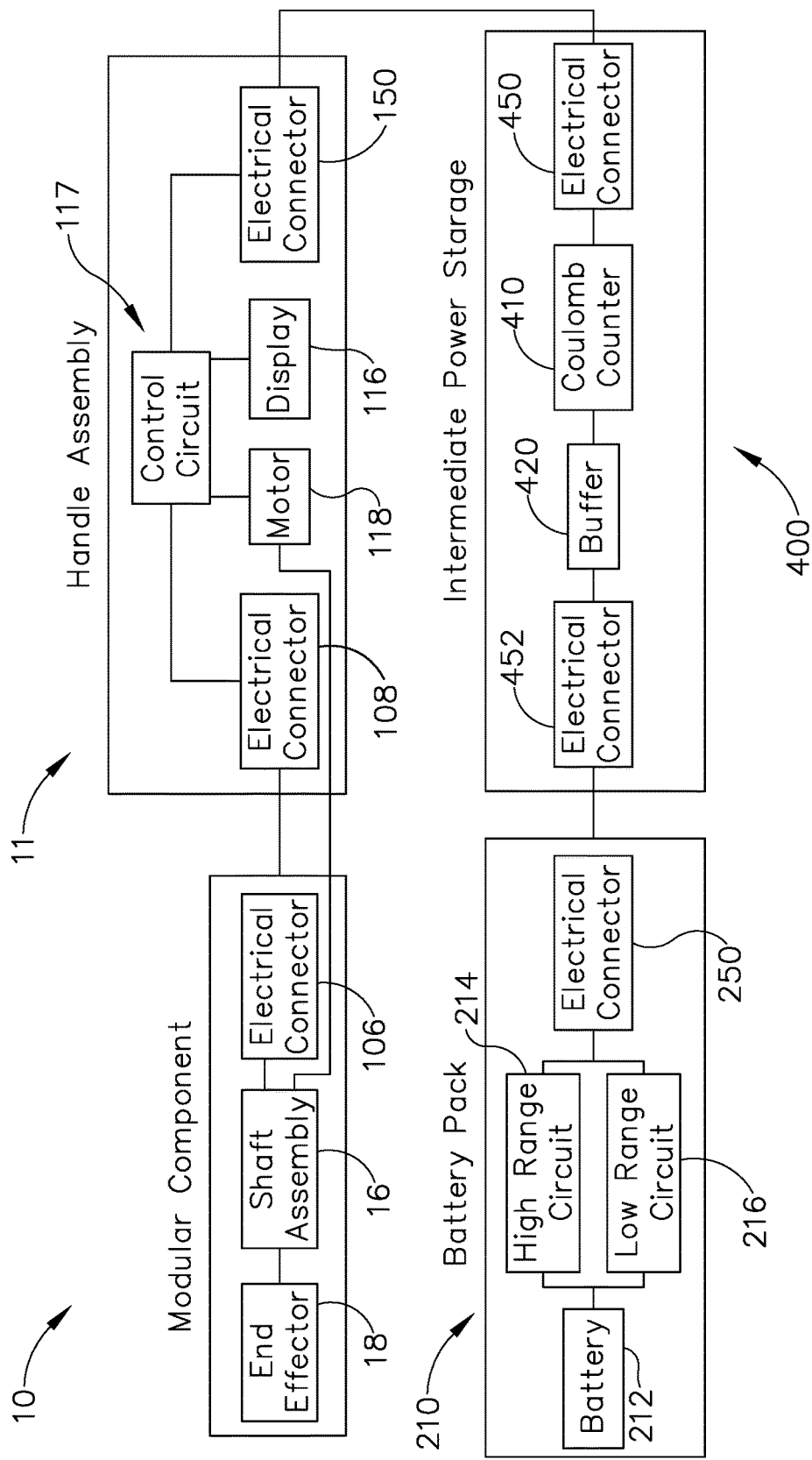
FIG. 9 depicts a block schematic view of an exemplary intermediate power storage device interconnected between the instrument of FIG. 1 and the battery pack of FIG. 7.

FIG. 9 shows an exemplary intermediate power storage (400) used with a battery powered surgical instrument (10) and a battery pack (210). In the present example, intermediate power storage (400) includes a coulomb counter (410) and a buffer (420). Intermediate power storage (400) is selectively installed between battery pack (210) and handle assembly (11) of surgical instrument (10). In particular, intermediate power storage (400) is electrically coupled to battery pack (210) through electrical connectors (250) and (452), respectively. Intermediate power storage (400) is electrically coupled to handle assembly (11) of surgical instrument (10) through electrical connectors (450) and (150), respectively. In other words, intermediate power storage (400) is in communication with both battery pack (210) and handle assembly (11). Therefore, in the present example, battery pack (210) is not in direct communication with surgical instrument (10).

Although not shown, intermediate power storage (400) may be integral with either handle assembly (11) or battery pack (210), such that intermediate power storage (400) is not a physically separate component between handle assembly (11) and battery pack (210). In this version, coulomb counter (410) and buffer (420) may be located within battery pack (210) or handle assembly (11) so long as they are positioned between battery (212) and control circuit (117). Furthermore, it should be understood that coulomb counter (410) and buffer (420) may be similarly incorporated into battery pack (110) which excludes the incorporation of power utilization circuits (214, 216) as are in battery pack (210).

Coulomb counter (410) is configured to electrically measure the quantity of electric charge contained within battery (212) and compare it to a predetermined threshold capacity necessary to operate surgical instrument (10). The predetermined threshold capacity is programmed in accordance with the highest power-demand load that may be drawn from handle assembly (11) to activate motor (118). Buffer (420) is configured to temporarily store the electric charge of battery (212) to thereby allow coulomb counter (410) to evaluate whether the stored electric charge in buffer (420) is sufficient for surgical instrument (10) to perform a complete firing sequence.

It should be understood that the predetermined threshold capacity may be programmed in intermediate power storage (400) in accordance with the particular surgical instrument (10) that intermediate power storage (400) will be utilized with. Alternatively, a control circuit (117) of handle assembly (11) may be programmed to communicate the predetermined threshold amount of power to intermediate power storage (400) once handle assembly (11) and intermediate power storage (400) are electrically coupled. As another variation, the predetermined threshold capacity may be based on the particular kind of shaft assembly (16, 120, 130, 140) that is coupled with handle assembly (11). Other suitable ways in which the predetermined threshold amount of power necessary to operate surgical instrument (10) may be communicated to intermediate power storage (400) will be apparent to those of ordinary skill in the art in view of the teachings herein. Further, although not shown, buffer (420) may comprise one or more supercapacitors. Other suitable components that may be used to form buffer (420) will be apparent to those of ordinary skill in the art in view of the teachings herein.

If coulomb counter (410) determines the measured power amount temporarily contained in buffer (420) satisfies the highest power-demand load for handle assembly (11) to perform an actuation of end effector (18) then intermediate power storage (400) may indicate to the operator through graphical user interface (116) that battery (212) contains adequate power to initiate a firing sequence. In this instance, handle assembly (11) obtains the necessary electrical power to perform the operation from battery pack (210) and through intermediate power storage (400). Once the actuation of end effector (18) is complete, coulomb counter (410) reassess the electric charge of battery (212) to determine whether battery (2.12) now contains the predetermined threshold amount necessary to subsequently operate surgical instrument (10).

If coulomb counter (410) detects an insufficient electric charge in buffer (420), intermediate power storage (400) may indicate to an operator that battery pack (210) does not contain sufficient power to perform a subsequent operation of surgical instrument (10) prior to the operator's attempted use of surgical instrument (10). In this instance, the charge stored in buffer (420) is sufficient to provide graphical user interface (116) with the necessary power to produce a warning indication to the operator. By providing a preliminary indication that battery pack (210) is not capable of providing surgical instrument (10) with the minimum amount of power necessary to perform a complete actuation of end effector (18), an operator may avoid the occurrence of initiating an actuation sequence that will ultimately be futile. As described above, the indication generated by intermediate power storage (400) may be displayed through graphical user interface (116) on handle assembly (11). However, as it would be apparent to those of ordinary skill in the art, other various forms of indication may be suitable and appropriate in view of the teachings herein.

Intermediate power storage (400) may be further configured to provide an electrical lockout that prevents the operator from actuating end effector (18) of surgical instrument (10) when coulomb counter (410) determines an insufficient amount of remaining power exists in buffer (420). In this instance, the operator's attempt to actuate end effector (18) will be unsuccessful as surgical instrument (10), in particular control circuit (117), are electrically locked out. Although not shown, for exemplary purposes only, intermediate power storage device (400) may include a display (not shown) that is configured to provide an operator an indication that battery pack (210) has insufficient power to allow surgical instrument (10) to complete an actuation of end effector (18). Furthermore, as another merely illustrative example, intermediate power storage device (400) may provide an audio signal to indicate the insufficiency of battery pack (210).

Figure 10:
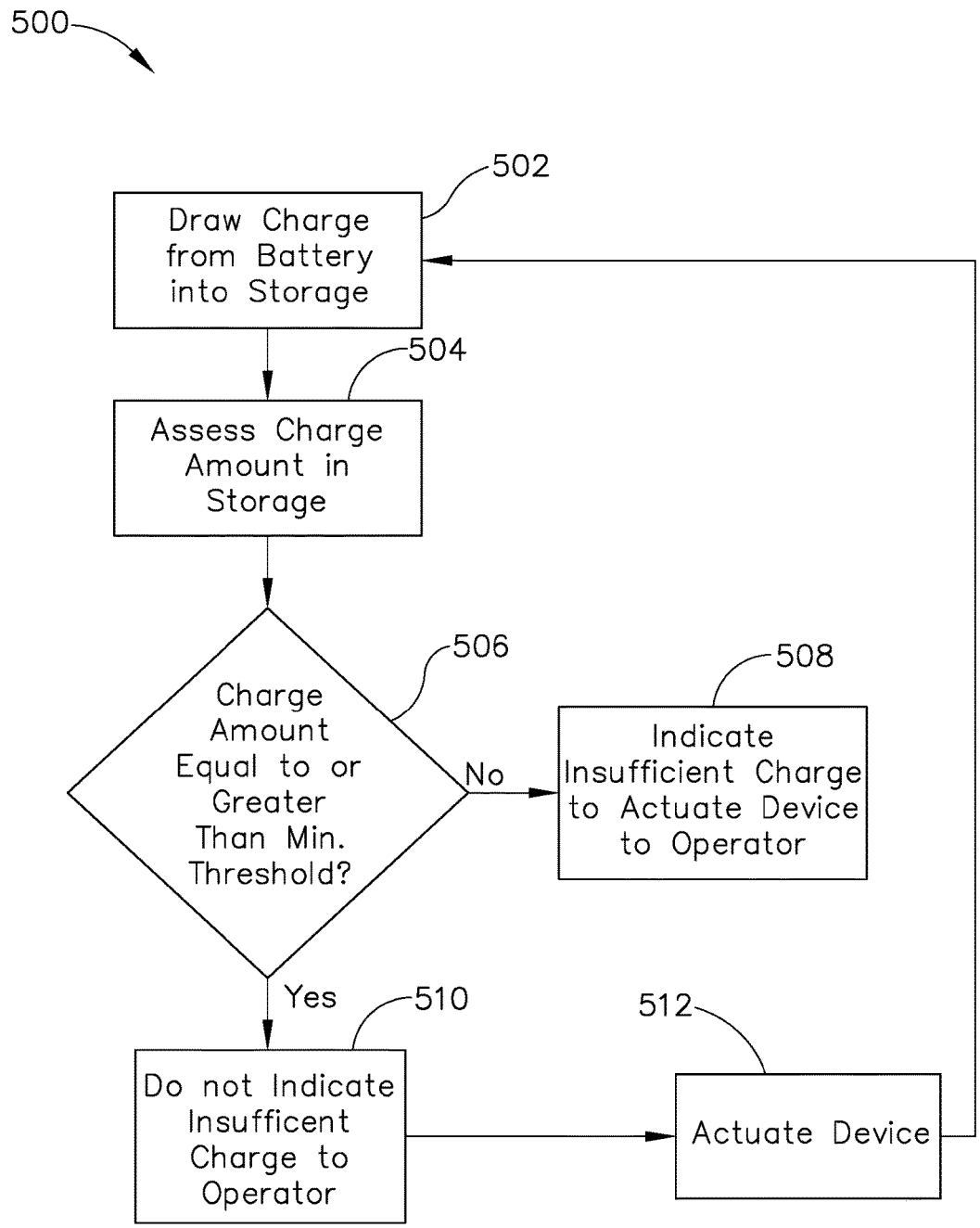
FIG. 10 depicts a flow diagram illustrating an algorithm utilized by the intermediate power storage device of FIG. 9 when determining whether adequate electric charge exists in the battery pack.

FIG. 10 depicts a flow diagram illustrating steps of a method (500) according to one embodiment of the invention for assessing the sufficiency of electric charge of battery (212) in a manner consistent with the disclosure above. The method (500) may be performed with battery pack (110, 210) or any suitable variation thereof. As described above, intermediate power storage device (400) may be installed between battery pack (210) and handle assembly (11) and comprises coulomb counter (410) and buffer (420). At step (502), buffer (420) draws and temporarily stores an electric charge emitted from battery (212) of battery pack (210). At step (504), coulomb counter (410) assess the quantity of electricity contained within buffer (420), for example in the manner described above. At step (506), coulomb counter (410) then determines whether the electric charge in buffer (420) is sufficient in comparison to the minimum power threshold required by surgical instrument (10) to perform a complete firing sequence of end effector (18). If the electric charge temporarily contained within buffer (420) does not exceed the power threshold required by surgical instrument (10), the system may proceed to step (508) where intermediate power storage (400) will transmit a signal to the operator to indicate the insufficient electric charge of battery (212). Alternatively, at step (510), where the quantity of electricity contained in buffer (420) does exceed the power threshold required by surgical instrument (10), the system may forego any indication to the operator of a lack of sufficient electric charge in battery (212). In this instance, intermediate power storage (400) may allow the operator to actuate surgical instrument (10) without interruption, as seen in step (512). Once control circuit (117) of surgical instrument (10) initiates an actuation of end effector (18), buffer (420) repetitively draws a subsequent electric charge from battery (212) to thereby allow coulomb counter (410) to reassess the remaining quantity of electricity contained in buffer (420) at step (502).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A battery pack of a surgical instrument, the battery pack comprising: (a) a battery; (b) a high range monitoring circuit, wherein the high range monitoring circuit is configured to be activated when an electrical current discharged from the battery exceeds a threshold, wherein the high range monitoring circuit is further configured to assess the electrical current discharged from the battery at a first rate; and (c) a low range monitoring circuit, wherein the low range monitoring circuit is configured to be activated when the electrical current discharged from the battery is below the threshold, wherein the low range monitoring circuit is further configured to assess the electrical current discharged from the battery at a second rate; wherein the battery is configured to conserve power when the low range monitoring circuit is activated; and wherein the low range monitoring circuit is configured to increase the second acquisition rate when the low range monitoring circuit remains activated for a predetermined duration; wherein the first rate is greater than the second rate.

EXAMPLE 2

The battery pack of a surgical instrument of Example 1, wherein the high range monitoring circuit is configured to adjust the first rate based on a power draw rate from the battery.

EXAMPLE 3

The battery pack of a surgical instrument of Example 2, wherein the high range monitoring circuit is configured to decrease the first rate when the power draw rate from the battery increases and increase the first rate when the power draw rate from the battery decreases.

EXAMPLE 4

The battery pack of a surgical instrument of any one or more of Examples 1 through 3, wherein the high range monitoring circuit is configured to activate when the power draw rate from the battery exceeds a predetermined threshold.

EXAMPLE 5

The battery pack of a surgical instrument of any one or more of Examples 1 through 4, wherein the low range monitoring circuit is configured to activate when the power draw rate from the battery is below the predetermined threshold.

EXAMPLE 6

The battery pack of a surgical instrument of any one or more of Examples 1 through 5, wherein the low range monitoring circuit includes a timing device configured to measure a time elapsed since activation of the low range monitoring circuit, wherein the timing device is operable to decrease the second rate when the low range monitoring circuit remains operational for a predetermined time.

EXAMPLE 7

The battery pack of a surgical instrument of any one or more of Examples 1 through 6, wherein the high range monitoring circuit includes a capacitor configured to store charge indicative of a power draw rate from the battery, wherein the battery pack is configured to display the power draw rate from the battery.

EXAMPLE 8

The battery pack of a surgical instrument of any one or more of Examples 1 through 7, wherein the first acquisition rate ranges between 1 measurement per second to 2000 measurements per second.

EXAMPLE 9

The battery pack of a surgical instrument of any one or more of Examples 1 through 8, wherein the second acquisition rate ranges between 1 measurement per minute to 1 measurement per hour.

EXAMPLE 10

The battery pack of a surgical instrument of any one or more of Examples 1 through 9, wherein the low range monitoring circuit is further operable to measure a temperature of the battery.

EXAMPLE 11

The battery pack of a surgical instrument of Example 10, wherein the low range power monitoring circuit is configured to determine a remaining charge of the battery based at least in part on the temperature measurement of the battery.

EXAMPLE 12

The battery pack of a surgical instrument of any one or more of Examples 1 through 11, wherein the low range monitoring circuit includes a counter, wherein the counter is configured to track time between uses of the battery.

EXAMPLE 13

The battery pack of a surgical instrument of Example 12, wherein the low range monitoring circuit is further configured to approximate a shelf life of the battery based at least in part on time tracked between uses of the battery.

EXAMPLE 14

The battery pack of a surgical instrument of any one or more of Examples 1 through 13, further comprising a capacitor electrically coupled to the high range monitoring circuit, wherein the capacitor is configured to receive electrical charge drawn from the battery.

EXAMPLE 15

The battery pack of a surgical instrument of Example 14, wherein the high range monitoring circuit is configured to determine a remaining charge of the battery based at least in part on the received electrical charge drawn from the battery.

EXAMPLE 16

A surgical instrument, comprising: (a) a body assembly, wherein the body assembly comprises an electrically powered component; and (b) a battery pack, wherein the battery pack has a remaining charge, wherein the battery pack is configured to electrically couple to the body assembly such that the battery pack provides power to the electrically powered component of the body assembly, wherein the battery pack comprises: (i) a first power circuit, wherein the first power circuit is configured to activate when the body assembly draws power from the battery above a threshold, wherein the first power circuit is operable to monitor the remaining charge of the battery pack at a first acquisition rate; and (ii) a second power circuit, wherein the second power circuit is configured to activate when the body assembly draws power from the battery less than the threshold, wherein the second power circuit is operable to monitor the remaining charge of the battery at a second acquisition rate, wherein the first acquisition rate is higher than the second acquisition rate; wherein the battery pack is configured to enter a sleep mode and preserve the remaining charge of the battery pack when the second power circuit is activated; and wherein the battery pack is configured to remain in the sleep mode until the first power circuit is activated.

EXAMPLE 17

The surgical instrument of Example 16, wherein the second power circuit is configured to decrease the second acquisition rate when the electrically powered component is not activated beyond a predetermined duration.

EXAMPLE 18

The surgical instrument of any one or more of Examples 16 through 17, wherein the second power circuit includes a timer configured to measure the elapsed time since the electrically powered component was activated, wherein the timer is configured to extend the low acquisition rate when the electrically powered component remains inactive beyond the time threshold.

EXAMPLE 19

The surgical instrument of any one or more of Examples 16 through 18, wherein the first power circuit is configured to decrease the high acquisition rate when the power provided from the battery pack increases and increase the high acquisition rate when the power provided from the battery pack decreases.

EXAMPLE 20

A method of monitoring the electrical charge of a battery of a surgical instrument, wherein the battery includes a high-power monitoring circuit configured to monitor the electrical charge of the battery at a high rate, wherein the battery includes a low-power monitoring circuit configured to monitor the electrical charge of the battery at a low rate, the method comprising: (a) identifying a power draw from the battery to the surgical instrument; (b) comparing the power draw to a predetermined limit; (c) assessing whether the power draw exceeds the predetermined limit; (d) activating the high-power monitoring circuit when the power draw exceeds the predetermined limit and reevaluating whether the power draw exceeds the predetermined limit at the high rate; or (e) activating the low-power monitoring circuit when the power draw is below the predetermined limit and reevaluating whether the power draw exceeds the predetermined limit at the low rate to conserve the electrical charge of the battery.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/634,385, entitled "Apparatus and Method to Determine End of Life of Battery Powered Surgical Instrument," filed on Jun. 27, 2017, published as U.S. Pub. No. 2018/0368821 on Dec. 27, 2018, the disclosure of which is incorporated by reference herein. Various suitable ways in which the teachings herein may be combined with the teachings of U.S. patent application Ser. No. 15/634,385, published as U.S. Pub. No. 2018/0368821 on Dec. 27, 2018, will be apparent to those of ordinary skill in the art in view of the teachings herein.

In addition to the foregoing, the teachings herein may be readily combined with the teachings of U.S. patent application Ser. No. 15/634,418, entitled "Surgical Instrument with Integrated and Independently Powered Displays," filed on Jun. 27, 2017, issued as U.S. Pat. No. 10,163,309 on Dec. 25, 2018, the disclosure of which is incorporated by reference herein. Various suitable ways in which the teachings herein may be combined with the teachings of U.S. patent application Ser. No. 15/634,418, issued as U.S. Pat. No. 10,163,309 on Dec. 25, 2018, will be apparent to those of ordinary skill in the art in view of the teachings herein.

In addition to the foregoing, the teachings herein may be readily combined with the teachings of U.S. patent application Ser. No. 15/634,436, entitled "Battery Pack with Integrated Circuit Providing Sleep Mode to Battery Pack and Associated Surgical Instrument," filed on Jun. 27, 2017, published as U.S. Pub. No. 2018/0368822 on Dec. 27, 2018, the disclosure of which is incorporated by reference herein. Various suitable ways in which the teachings herein may be combined with the teachings of U.S. patent application Ser. No. 15/634,436, published as U.S. Pub. No. 2018/0368822 on Dec. 27, 2018, will be apparent to those of ordinary skill in the art in view of the teachings herein.

In addition to the foregoing, the teachings herein may be readily combined with the teachings of U.S. patent application Ser. No. 15/634,475, entitled "Powered Surgical instrument with Latching Feature Preventing Removal of Battery Pack," filed on Jun. 27, 2017, published as U.S. Pub. No. 2018/0368848 on Dec. 27, 2018, the disclosure of which is incorporated by reference herein. Various suitable ways in which the teachings herein may be combined with the teachings of U.S. patent application Ser. No. 15/634,475, published as U.S. Pub. No. 2018/0368848 on Dec. 27, 2018, will be apparent to those of ordinary skill in the art in view of the teachings herein.

In addition to the foregoing, the teachings herein may be readily combined with the teachings of U.S. patent application Ser. No. 15/634,497, entitled "Modular Powered Electrical Connection for Surgical Instrument with Features to Prevent Electrical Discharge" filed on Jun. 27, 2017, published as U.S. Pub. No. 2018/0368849 on Dec. 27, 2018, the disclosure of which is incorporated by reference herein. Various suitable ways in which the teachings herein may be combined with the teachings of U.S. patent application Ser. No. 15/634,497, published as U.S. Pub. No. 2018/0368849 on Dec. 27, 2018, will be apparent to those of ordinary skill in the art in view of the teachings herein.

In addition to the foregoing, the teachings herein may be readily combined with the teachings of U.S. patent application Ser. No. 15/634,524, published as U.S. Pub. No. 2018/0368850 on Dec. 27, 2018, entitled "Powered Surgical Instrument with Independent Selectively Applied Rotary and Linear Drivetrains," filed on Jun. 27, 2017, the disclosure of which is incorporated by reference herein. Various suitable ways in which the teachings herein may be combined with the teachings of U.S. patent application Ser. No. 15/634,524, published as U.S. Pub. No. 2018/0368850 on Dec. 27, 2018, will be apparent to those of ordinary skill in the art in view of the teachings herein.

In addition to the foregoing, the teachings herein may be readily combined with the teachings of U.S. patent application Ser. No. 15/634,556, published as U.S. Pub. No. 2018/0368851 on Dec. 27, 2018, entitled "Powered Circular Stapler with Reciprocating Drive Member to Provide Independent Stapling and Cutting of Tissue," filed on Jun. 27, 2017, the disclosure of which is incorporated by reference herein. Various suitable ways in which the teachings herein may be combined with the teachings of U.S. patent application Ser. No. 15/634,556, published as U.S. Pub. No. 2018/0368851 on Dec. 27, 2018, will be apparent to those of ordinary skill in the art in view of the teachings herein.

In addition to the foregoing, the teachings herein may be readily combined with the teachings of U.S. patent application Ser. No. 15/634,620, published as a U.S. Pub. No. 2018/0368836 on Dec. 27, 2018, entitled "Surgical Stapler with Independently Actuated Drivers to Provide Varying Staple Heights," filed on Jun. 27, 2017, the disclosure of which is incorporated by reference herein. Various suitable ways in which the teachings herein may be combined with the teachings of U.S. patent application Ser. No. 15/634,620, published as U.S. Pub. No. 2018/0368836 on Dec. 27, 2018, will be apparent to those of ordinary skill in the art in view of the teachings herein.

In addition to the foregoing, the teachings herein may be readily combined with the teachings of U.S. patent application Ser. No. 15/634,589, issued as U.S. Pat. No. 10,090,616 on Oct. 2, 2018, entitled "Surgical Instrument Handle Assembly with Feature to Clean Electrical Contacts at Modular Shaft Interface," filed on Jun. 27, 2017, the disclosure of which is incorporated by reference herein. Various suitable ways in which the teachings herein may be combined with the teachings of U.S. patent application Ser. No. 15/634,589, issued as U.S. Pat. No. 10,090,616 on Oct. 2, 2018, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A battery pack of a surgical instrument, the battery pack comprising:
   (a) a battery;
   (b) a high range monitoring circuit, wherein the high range monitoring circuit is configured to be activated when an electrical current discharged from the battery exceeds a predetermined threshold value, wherein the high range monitoring circuit is further configured to assess the electrical current discharged from the battery at a first acquisition rate; and
   (c) a low range monitoring circuit, wherein the low range monitoring circuit is configured to be activated when the electrical current discharged from the battery is below the predetermined threshold value, wherein the low range monitoring circuit is further configured to assess the electrical current discharged from the battery at a second acquisition rate;
   wherein the battery is configured to conserve power when the low range monitoring circuit is activated; and
   wherein the low range monitoring circuit is configured to decrease the second acquisition rate when the low range monitoring circuit remains activated for a predetermined duration;
   wherein the first acquisition rate is greater than the second acquisition rate.

2. The battery pack of a surgical instrument of claim 1, wherein the high range monitoring circuit is configured to adjust the first acquisition rate based on a power draw rate from the battery.

3. The battery pack of a surgical instrument of claim 2, wherein the high range monitoring circuit is configured to decrease the first acquisition rate when the power draw rate from the battery increases and increase the first acquisition rate when the power draw rate from the battery decreases.

4. The battery pack of a surgical instrument of claim 2, wherein the high range monitoring circuit is configured to activate when the power draw rate from the battery exceeds a predetermined threshold rate.

5. The battery pack of a surgical instrument of claim 4, wherein the low range monitoring circuit is configured to activate when the power draw rate from the battery is below the predetermined threshold rate.

6. The battery pack of a surgical instrument of claim 1, wherein the low range monitoring circuit includes a timing device configured to measure a time elapsed since activation of the low range monitoring circuit, wherein the timing device is operable to decrease the second acquisition rate when the low range monitoring circuit remains operational for a predetermined time.

7. The battery pack of a surgical instrument of claim 1, wherein the high range monitoring circuit includes a capacitor configured to store charge indicative of a power draw rate from the battery, wherein the battery pack is configured to display the power draw rate from the battery.

8. The battery pack of a surgical instrument of claim 1, wherein the first acquisition rate ranges between 1 measurement per second to 2000 measurements per second.

9. The battery pack of a surgical instrument of claim 1, wherein the second acquisition rate ranges between 1 measurement per minute to 1 measurement per hour.

10. The battery pack of a surgical instrument of claim 1, wherein the low range monitoring circuit is further operable to measure a temperature of the battery.

11. The battery pack of a surgical instrument of claim 10, wherein the low range monitoring circuit is configured to determine a remaining charge of the battery based at least in part on the temperature measurement of the battery.

12. The battery pack of a surgical instrument of claim 1, wherein the low range monitoring circuit includes a clock, wherein the low range monitoring circuit includes a counter, wherein the counter is configured to track time between uses of the battery.

13. The battery pack of a surgical instrument of claim 12, wherein the low range monitoring circuit is further configured to approximate a shelf life of the battery based at least in part on time tracked between uses of the battery.

14. The battery pack of a surgical instrument of claim 1, further comprising a capacitor electrically coupled to the high range monitoring circuit, wherein the capacitor is configured to receive electrical charge drawn from the battery.

15. The battery pack of a surgical instrument of claim 14, wherein the high range monitoring circuit is configured to determine a remaining charge of the battery based at least in part on the received electrical charge drawn from the battery.

16. A surgical instrument, comprising:
   (a) a body assembly, wherein the body assembly comprises an electrically powered component; and
   (b) a battery pack, wherein the battery pack has a remaining charge, wherein the battery pack is configured to electrically couple to the body assembly such that the battery pack provides power to the electrically powered component of the body assembly, wherein the battery pack comprises:
      (i) a first power circuit, wherein the first power circuit is configured to activate when the body assembly draws power from the battery above a predetermined threshold value, wherein the first power circuit is operable to monitor the remaining charge of the battery pack at a first acquisition rate; and
      (ii) a second power circuit, wherein the second power circuit is configured to activate when the body assembly draws power from the battery less than the predetermined threshold value, wherein the second power circuit is operable to monitor the remaining charge of the battery at a second acquisition rate, wherein the first acquisition rate is higher than the second acquisition rate;
   wherein the battery pack is configured to enter a sleep mode and preserve the remaining charge of the battery pack when the second power circuit is activated;
   wherein the second power circuit is configured to decrease the second acquisition rate when the second power circuit remains activated for a predetermined duration; and wherein the battery pack is configured to remain in the sleep mode until the first power circuit is activated.

17. The surgical instrument of claim 16, wherein the second power circuit is configured to decrease the second acquisition rate when the electrically powered component is not activated beyond a predetermined duration.

18. The surgical instrument of claim 16, wherein the second power circuit includes a timer configured to measure the elapsed time since the electrically powered component was activated, wherein the timer is configured to decrease the second acquisition rate when the electrically powered component remains inactive beyond a time threshold.

19. The surgical instrument of claim 16, wherein the first power circuit is configured to decrease the first acquisition rate when the power provided from the battery pack increases and increase the first acquisition rate when the power provided from the battery pack decreases.

20. A method of monitoring the electrical charge of a battery of a surgical instrument, wherein the battery includes a high-power monitoring circuit configured to monitor the electrical charge of the battery at a first acquisition rate, wherein the battery includes a low-power monitoring circuit configured to monitor the electrical charge of the battery at a second acquisition rate lower than the first acquisition rate, wherein the low-power monitoring circuit is configured to decrease the second acquisition rate when the low-power monitoring circuit remains activated for a predetermined duration, the method comprising:
   (a) identifying an electrical current discharge from the battery of the surgical instrument;
   (b) assessing whether the electrical current discharge exceeds the predetermined threshold value; and
   (c) based on the assessment, performing at least one of the following steps:
      (i) activating the high-power monitoring circuit when the electrical current discharge exceeds a predetermined threshold value, and subsequently reassessing at the high acquisition rate whether the electrical current discharge exceeds the predetermined threshold value, or
      (ii) activating the low-power monitoring circuit when the electrical current discharge is below the predetermined threshold value, and subsequently reassessing at the low acquisition rate whether the electrical current discharge exceeds the predetermined threshold value.

\* \* \* \* \*